(12) United States Patent
Baba et al.

(10) Patent No.: US 11,004,669 B2
(45) Date of Patent: May 11, 2021

(54) METHOD AND APPARATUS FOR ANALYZING SAMPLES USING MASS SPECTROMETRY

(71) Applicant: DH Technologies Development Pte. Ltd., Singapore (SG)

(72) Inventors: Takashi Baba, Richmond Hill (CA); Paul Baker, Pittsburgh, PA (US); John Lawrence Campbell, Milton (CA); Yves Le Blanc, Newmarket (CA)

(73) Assignee: DH Technologies Development Pte. Ltd., Singapore (SG)

( * ) Notice: Subject to any disclaimer, the term of this patent is extended or adjusted under 35 U.S.C. 154(b) by 285 days.

(21) Appl. No.: 16/063,104

(22) PCT Filed: Dec. 15, 2016

(86) PCT No.: PCT/IB2016/057691
§ 371 (c)(1),
(2) Date: Jun. 15, 2018

(87) PCT Pub. No.: WO2017/103860
PCT Pub. Date: Jun. 22, 2017

(65) Prior Publication Data
US 2020/0279727 A1    Sep. 3, 2020

Related U.S. Application Data

(60) Provisional application No. 62/268,912, filed on Dec. 17, 2015, provisional application No. 62/329,679, filed on Apr. 29, 2016.

(51) Int. Cl.
*H01J 49/00*    (2006.01)
*G01N 33/92*    (2006.01)

(52) U.S. Cl.
CPC .......... *H01J 49/0072* (2013.01); *G01N 33/92* (2013.01); *H01J 49/0054* (2013.01)

(58) Field of Classification Search
CPC .... H01J 49/26; H01J 49/0072; H01J 49/0054; G01N 33/92; G01N 33/00; G01N 33/48; G01N 33/50
(Continued)

(56) References Cited

U.S. PATENT DOCUMENTS 9,347,917 B2 * 5/2016 Campbell ........... H01J 49/0031
9,360,455 B2 * 6/2016 Campbell ........... H01J 49/0422
(Continued)

OTHER PUBLICATIONS

International Search Report and Written Opinion for PCT/US2016/057691 dated Feb. 10, 2017.
(Continued)

*Primary Examiner* — Nicole M Ippolito

(57) ABSTRACT

A method and apparatus for analyzing samples using mass spectrometry are disclosed. The apparatus includes a reaction device configured to dissociate sample ions into fragments by reacting the sample ions with a charged species (e.g., electrons) such as through ECD, EID, or EIEIO. The kinetic energy of the charged species is such that the fragments may be detected and produce spectra that allow for the determination of isomeric species in the sample and the location of double bonds and/or the orientation of those double bonds within the sample molecules. The fragments may include radical fragments and non-radical fragments. Spectra resulting from analysis of the fragments may allow for the determination of the oxygen-radical fragments resulting from the dissociation of the sample molecules as confirmation of the presence of those radical fragments.

20 Claims, 35 Drawing Sheets

(58) Field of Classification Search
USPC .......................... 250/281, 282, 283, 287, 288
See application file for complete search history.

(56) References Cited

U.S. PATENT DOCUMENTS

2009/0134323 A1  5/2009  Gross et al.
2015/0316507 A1  11/2015 Campbell et al.

OTHER PUBLICATIONS

Maccarone et al., 'Characterization of acyl chain position in unsaturated phosphatidylcholines using differential mobility mass spectrometry' Journal of Lipid Research, vol. 55, pp. 1668-1677 (2014).

Sullards et al., 'Analysis of mammalian sphingolipids by liquid chromatography tandem mass spectrometry (LC-MS/MS) and tissue imaging mass spectrometry (TIMS)' Biochimica et Biophysica Acta (BBA)—Molecular and Cell Biology of Lipids, Vo. 1811, pp. 838-853 (2011).

Trimpin et al., 'Profiling of phospholipids and related lipid structures using multidimensional ion mobility spectrometry' International Journal of Mass Spectrometry, vol. 287, pp. 58-69 (2009).

Baba et al., 'In-depth sphingomyelin characterization using electron impact excitation of ions from organics and mass spectrometry' Journal of Lipid Research, vol. 57, No. 5 pp. 858-867 (ASBMB version, internal pp. 1-35) (May 2016).

Baba et al., 'Structural identification of triacylglycerol isomers using electron impact excitation of ions from organics (EIEIO)' Journal of Lipid Research, vol. 57, No. 11, pp. 2015-2027 (ASBMB version, internal pp. 1-35) (Nov. 2016).

* cited by examiner

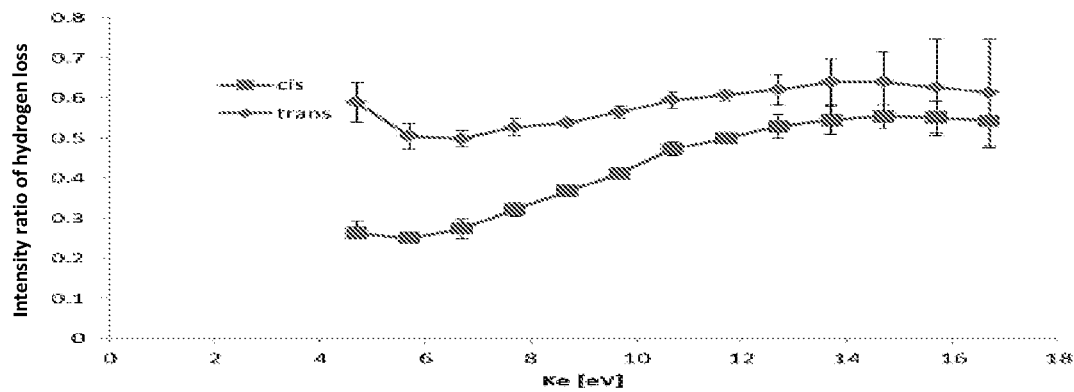
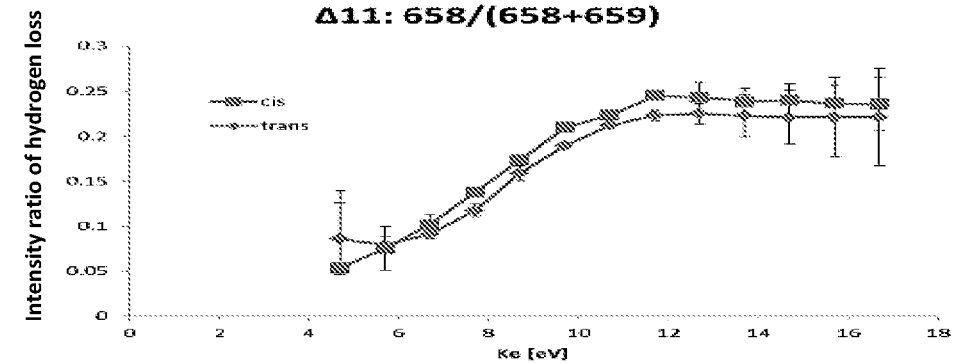
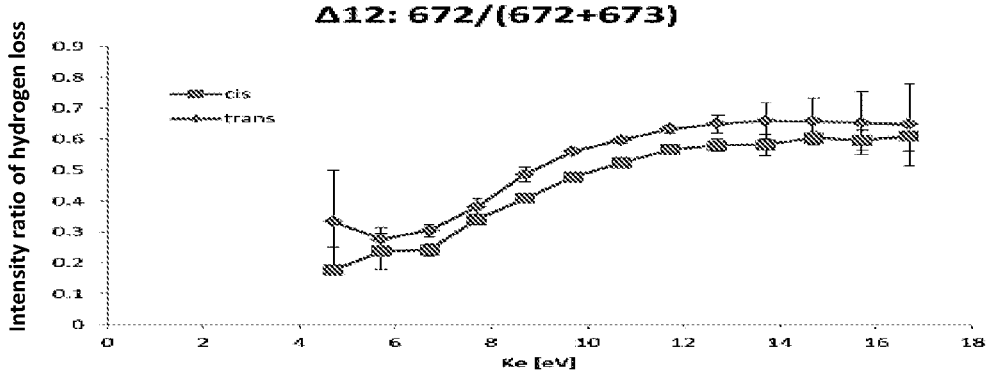
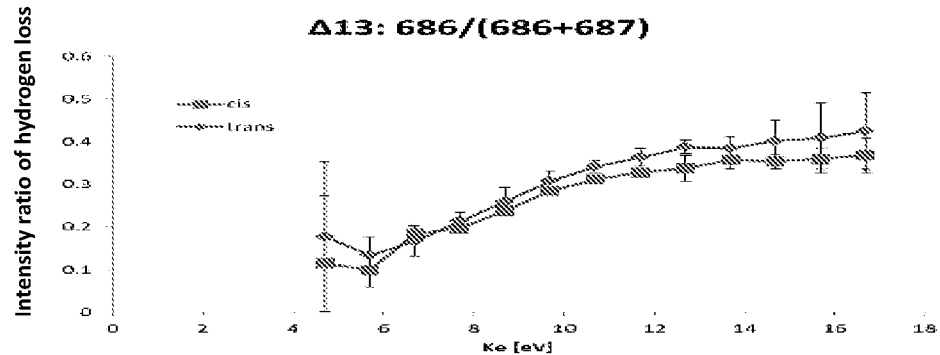
FIG. 2C

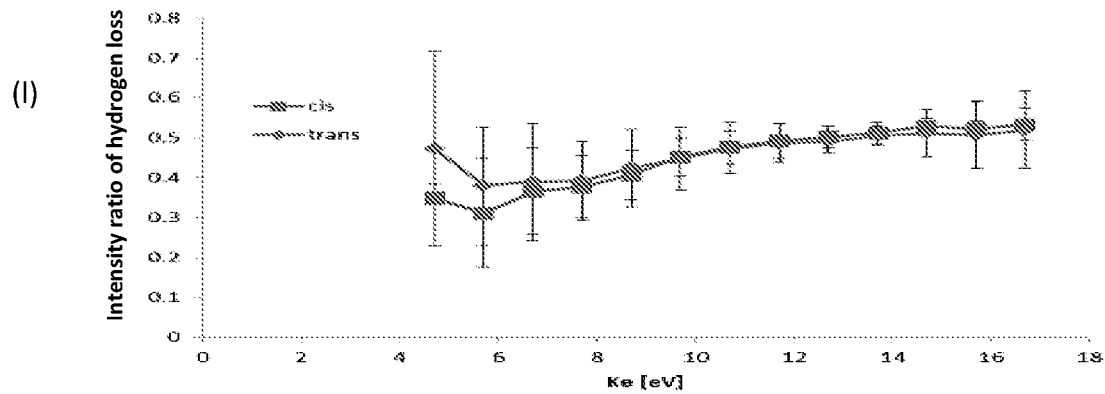
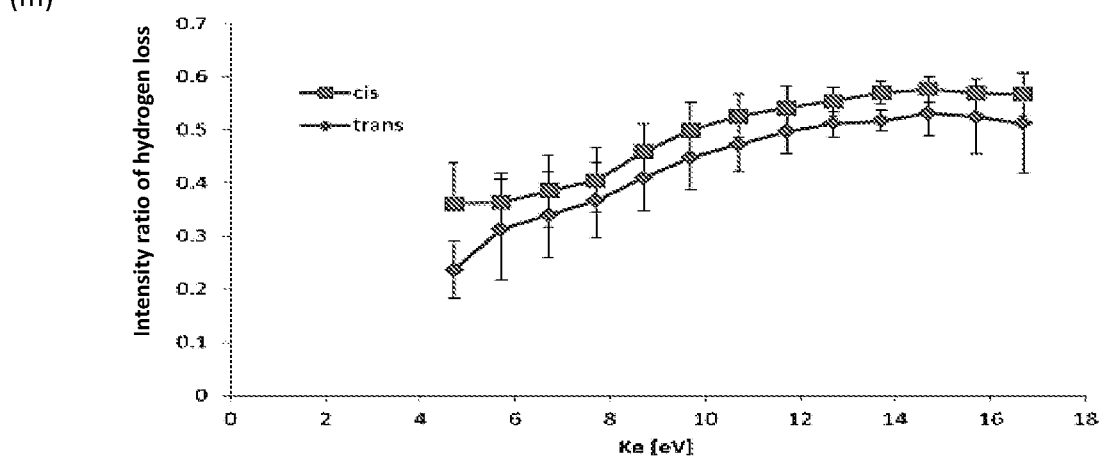
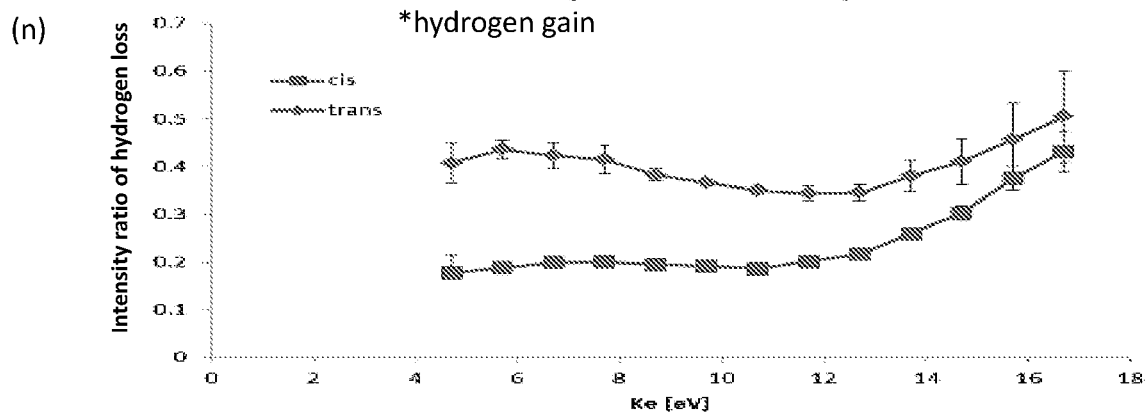
FIG. 2D

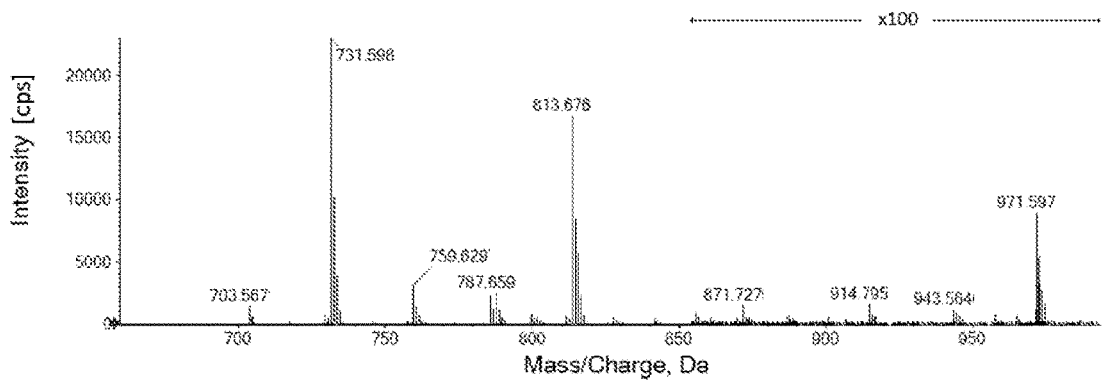

| precursor m/z | precursor intensity [%] | identified sphingomyelins | | | |
|---|---|---|---|---|---|
| 675.505 | 0.15 | SM(d18:1,14:0) [90%] | | | |
| 689.52 | 0.03 | SM(d17:1,16:0) [73%] | SM(d18:1,15:0) [27%] | | |
| 701.52 | 0.04 | SM(d18:2,16:0) [92%] | | | |
| 703.535 | 2.68 | SM(d18:1,16:0) [79%] | SM(d16:1,18:0) [21%] | | |
| 717.55 | 0.29 | SM(d17:1,18:0) [46%] | SM(d18:1,17:0) [45%] | SM(d19:1,16:0) [4%] | SM(d16:1,19:0) [3%] |
| 729.551 | 1.69 | SM(d18:2,18:0) [85%] | SM(d18:1,18:1(n-9)) [10%] | | |
| 731.539 | 40.77 | SM(d18:1,18:0) [94%] | | | |
| 743.564 | 0.04 | SM(d19:2,18:0) [81%] | | | |
| 759.589 | 6.56 | SM(d20:1,18:0) [52%] | SM(d18:1,20:0) [44%] | | |
| 771.595 | 0.03 | SM(d18:1,21:1(n-7)) [33%] | SM(d17:1,22:1(n-7)) [25%] | SM(d16:1,23:1(n-7)) [24%] | SM(d18:2,21:0) [11%] |
| 783.594 | 0.15 | SM(d18:1,22:2(n-6,-9)) [84%] | SM(d18:2,22:1(n-6)) [16%] | | |
| 785.604 | 4.82 | SM(d18:1,22:1(n-6)) [95%] | | | |
| 787.616 | 5.45 | SM(d18:1,22:0) [83%] | SM(d18:0,22:1(n-6)) [11%] | | |
| 797.61 | 0.06 | SM(d18:1,23:2) [64%] | | | |
| 799.622 | 1.52 | SM(d18:1,23:1(n-7)) [89%] | | | |
| 801.635 | 1.26 | SM(d18:1,23:0) [83%] | SM(d18:0,23:1) [10%] | | |
| 809.607 | 0.06 | SM(d18:1,24:3(n-6,*,*)) [80%] | | | |
| 811.622 | 1.55 | SM(d18:1,24:2(n-6,-9)) [82%] | SM(d18:2,24:1(n-9)) [10%] | SM(d18:2,24:1(n-6)) [4%] | |
| 813.605 | 29.99 | SM(d18:1,24:1(n-9)) [81%] | SM(d18:1,24:1(n-6)) [13%] | | |
| 825.636 | 0.11 | SM(d18:1,25:2(n-6,-9)) [75%] | | | |
| 827.649 | 0.89 | SM(d18:1,25:1) [89%] | SM(d19:1,24:1) [11%] | | (n-6)[17%], (n-9)[83%] |
| 837.636 | 0.03 | SM(d18:1,26:3(n-6,*,*)) [51%] | SM(d18:1,26:3(n-9,*,*)) [38%] | | |
| 839.65 | 0.16 | SM(d18:1,26:2(n-6,-9)) [52%] | SM(d18:1,26:2(n-9,-12)) [17%] | SM(d20:2,24:1(n-9)) [9%] | SM(d20:2,24:1(n-6)) [6%] |
| 841.663 | 0.88 | SM(d18:1,26:1) [80%] | SM(d20:1,24:1) [14%] | | (n-6)[31%], (n-9)[69%] |
| 855.678 | 0.01 | SM(d20:1,25:1) [55%] | SM(d18:1,27:1) [32%] | SM(d19:1,26:1) [13%] | |
| 869.693 | 0.01 | SM(d18:1,28:1) [100%] | | | |
| 871.69 | 0.03 | SM(d18:1,24:1) + 58.05 [100%] | | | |
| 873.692 | 0.01 | SM(d18:2,24:1) + 58.05 [100%] | | | |
| 887.471 | 0.01 | SM(d18:1,21:1) + 101.11 [100%] | | | |
| 914.744 | 0.01 | SM(d18:1,18:0) with CH3IO | SM(d18:1,24:1) + 101.11 | | |
| 943.523 | 0.04 | SM(d18:1,22:0) with CH3IO [100%] | | | |
| 957.609 | 0.01 | SM(d18:1,23:0) with CH3IO [100%] | | | |
| 971.551 | 0.19 | SM(d18:1,24:0) with CH3IO [100%] | | | |

FIG. 18

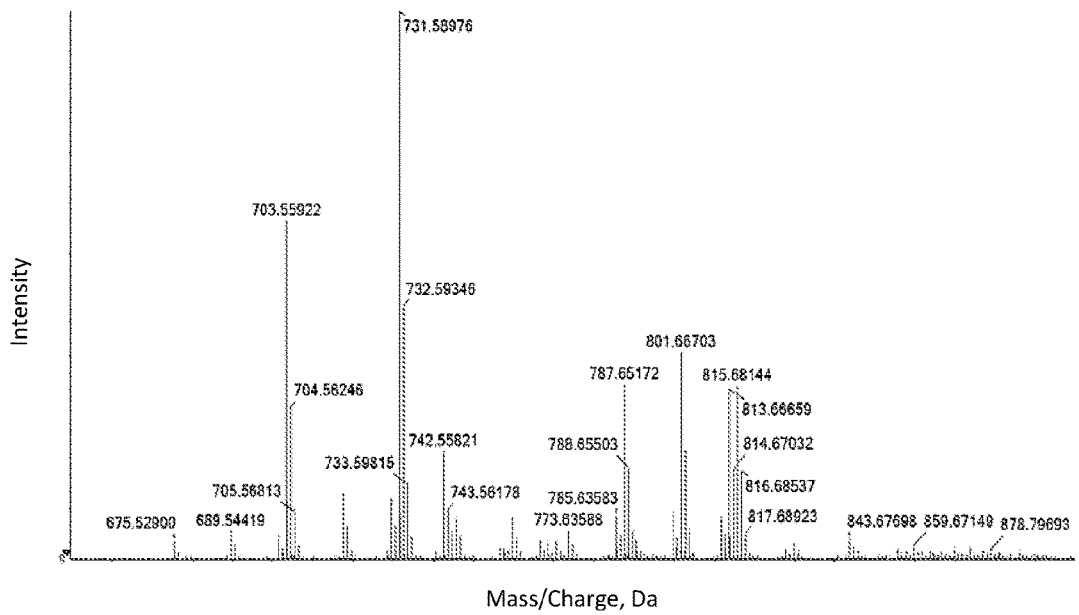

| precursor m/z | concentration [uM] | weight [%] in total | identified sphingomyelins | | |
|---|---|---|---|---|---|
| 675.511 | 0.029 | 0.008 | SM(d16:1,16:0) [70%] (46 sec) | | |
| 689.526 | 0.061 | 0.017 | SM(d17:1,16:0) [100%] (14 sec) | | |
| 701.526 | 0.050 | 0.014 | SM(d18:2,16:0) [manual] | | |
| 703.546 | 0.660 | 0.186 | SM(d18:1,16:0) [95%] (0.086 sec) | SM(d16:1,18:0) [5%] (5 sec) | |
| 717.557 | 0.132 | 0.038 | SM(d17:1,18:0) [100%] (3 sec) | | |
| 729.555 | 0.128 | 0.037 | SM(d18:2,18:0) [66%] (11 sec) | SM(d18:1,18:1(n-9)) [34%] (11 sec) | |
| 731.572 | 1.158 | 0.339 | SM(d18:1,18:0) [100%] (0.032 sec) | | |
| 745.577 | 0.120 | 0.036 | SM(d19:1,18:0) [77%] (4 sec) | SM(d18:1,19:0) [23%] (6 sec) | |
| 759.588 | 0.112 | 0.034 | SM(d18:1,20:0) [88%] (4 sec) | | |
| 773.607 | 0.068 | 0.021 | SM(d17:1,22:0) [48%] (11 sec) | SM(d18:1,21:0) [30%] (11 sec) | SM(d16:1,23:0) [22%] (17 sec) |
| 785.609 | 0.094 | 0.029 | SM(d18:1,22:1) [54%] (14 sec) | SM(d18:2,22:0) [46%] (14 sec) | |
| 787.63 | 0.410 | 0.129 | SM(d18:1,22:0) [92%] (0.346 sec) | SM(d17:1,23:0) [8%] (2 sec) | |
| 799.624 | 0.108 | 0.035 | SM(d18:2,23:0) [44%] (19 sec) | SM(d18:1,23:1) [30%] (19 sec) | SM(d17:1,24:1) [26%] (19 sec) |
| 801.643 | 0.472 | 0.151 | SM(d18:1,23:0) [87%] (0.220 sec) | SM(d19:1,22:0) [7%] (8 sec) | SM(d17:1,24:0) [6%] (2 sec) |
| 811.623 | 0.098 | 0.032 | SM(d18:1,24:2(n-6,-9)) [78%] (14 sec) | SM(d18:2,24:1(n-9)) [22%] (28 sec) | |
| 813.644 | 0.376 | 0.122 | SM(d18:1,24:1(n-9)) [80%] (0.549 sec) | SM(d18:2,24:0) [20%] (2 sec) | |
| 815.655 | 0.425 | 0.139 | SM(d18:1,24:0) [91%] (0.278 sec) | SM(d19:1,23:0) [9%] (5 sec) | |
| 827.628 | 0.021 | 0.007 | PC head group, but may not be a SM. | | |
| 829.649 | 0.049 | 0.016 | SM(d19:1,24:0) [51%] (19 sec) | SM(d18:1,25:0) [49%] (19 sec) | |
| 843.636 | 0.041 | 0.014 | PC(17:0,16:3) + 101.11 | | |
| 855.605 | 0.028 | 0.010 | PC(17:0,16:3) + 113.05 | | |

FIG. 19

| precursor m/z | precursor intensity [%] | | | identified sphingomyelins | | | |
|---|---|---|---|---|---|---|---|
| 647.486 | 0.16 | SM{d16:1,14:0} [100%] | | | | | |
| 661.502 | 0.16 | SM{d17:1,14:0} [78%] | SM{d16:1,15:0} [22%] | | | | |
| 673.501 | 0.04 | SM{d18:2,14:0} [52%] | SM{d16:1,16:1} [48%] | | | | |
| 675.508 | 3.98 | SM{d16:1,16:0} [72%] | SM{d18:1,14:0} [24%] | SM{d17:1,15:0} [5%] | | | |
| 685.511 | 0.05 | PC head group, but may not be a SM. | | | | | |
| 687.517 | 0.07 | SM{d17:1,16:1} [100%] | | | | | |
| 689.524 | 2.84 | SM{d17:1,16:0} [83%] | SM{d18:1,15:0} [13%] | | | | |
| 699.515 | 0.02 | SM{d11:1,18:2} [100%] | | | | | |
| 703.53 | 15.89 | SM{d18:1,16:0} [91%] | SM{d19:1,15:0} [9%] | | | | |
| 713.544 | 0.08 | SM{d17:1,18:1} [57%] | SM{d19:2,16:0} [29%] | | | | |
| 717.556 | 1.07 | SM{d19:1,16:0} [43%] | SM{d18:1,17:0} [29%] | SM{d17:1,18:0} [22%] | SM{d20:1,15:0} [4%] | SM{d16:1,19:0} [3%] | |
| 727.542 | 0.02 | SM{d18:1,18:2} [100%] | SM{d16:1,20:0} [16%] | | | | |
| 731.569 | 1.58 | SM{d18:1,18:0} [79%] | | | | | |
| 741.581 | 0.03 | PC head group | | | | | |
| 743.576 | 0.04 | SM{d19:1,18:1} [84%] | | | | | |
| 745.586 | 0.59 | SM{d16:1,21:0} [15%] | SM{d19:1,18:0} [23%] | SM{d17:1,20:0} [14%] | SM{d18:1,19:0} [8%] | | |
| | | PC_HG, but may not be a SM | | | | | |
| 755.591 | 0.06 | SM{d16:1,22:1} [81%] | SM{d18:1,20:1} [9%] | SM{d18:2,20:0} [5%] | | | |
| 757.59 | 0.22 | SM{d16:1,22:0} [88%] | SM{d17:1,21:0} [7%] | SM{d18:1,20:0} [4%] | | {n-7}[84%],{n-9}[16%] | |
| 759.588 | 6.84 | SM{d16:1,23:2} [100%] | | | | | |
| 769.573 | 0.09 | SM{d16:1,23:1} [93%] | SM{d17:1,22:1} [7%] | | | | |
| 773.596 | 2.13 | SM{d16:1,23:0} [79%] | SM{d17:1,22:0} [17%] | SM{d18:1,21:0} [4%] | | {n-6}[21%],{n-9}[79%] | |
| 783.608 | 12.23 | SM{d16:1,24:2(n-9,?)} [79%] | SM{d18:1,22:2(n-9,?)} [13%] | | | | |
| | 0.16 | | SM{d18:1,23:1(n-9)} | | | | |
| 785.609 | 2.73 | SM{d16:1,24:1(n-9)} [61%] | [22%] | SM{d18:1,22:1(n-9)} [9%] | SM{d18:2,22:0} [8%] | | |
| 787.61 | 15.75 | SM{d18:1,22:0} [44%] | SM{d16:1,24:0} [39%] | SM{d17:1,23:0} [17%] | | | |
| 789.621 | 4.09 | SM{d18:0,22:0} [manual] | | | | | |
| 797.623 | 0.16 | SM{d18:2,23:1(n-9)} [56%] | SM{d17:1,24:2} [19%] | SM{d18:1,23:2} [14%] | SM{d16:1,25:2} [11%] | | |
| 799.62 | 3.93 | SM{d18:1,23:1} [58%] | SM{d16:1,25:1} [20%] | SM{d17:1,24:1} [10%] | SM{d18:2,23:0} [7%] | | |
| 801.631 | 12.64 | SM{d18:1,23:0} [77%] | SM{d17:1,24:0} [12%] | SM{d19:1,22:0} [12%] | | {n-6}[6%],{n-9}[94%] | |
| | | | SM{d18:2,24:1(n-9)} | | | | |
| 811.633 | 0.15 | SM{d18:1,24:2} [63%] | [32%] | | | | |
| | | | SM{d19:1,23:1(n-9)} | | | | |
| 813.637 | 2.47 | SM{d18:1,24:1(n-9)} [71%] | [14%] | SM{d18:2,24:0} [8%] | SM{d17:1,25:1(n-9)} [7%] | | |
| 825.641 | 7.59 | SM{d18:1,24:0} [80%] | SM{d19:1,23:0} [20%] | SM{d20:2,23:1} [19%] | | | |
| 825.642 | 0.07 | SM{d18:2,25:1} [39%] | SM{d19:1,24:2} [21%] | SM{d20:2,23:0} [12%] | | | |
| 829.667 | 1.34 | SM{d19:1,24:0} [52%] | SM{d18:1,25:0} [33%] | | | | |
| 841.674 | 0.13 | SM{d19:1,25:1(n-9)} [53%] | SM{d20:2,24:0} [30%] | SM{d20:1,24:1(n-9)} [16%] | | | |
| 843.686 | 0.25 | SM{d18:1,26:0} [49%] | SM{d20:1,24:0} [30%] | SM{d19:1,25:0} [21%] | | | |
| 847.657 | 0.05 | SM possible | | | | | |
| 849.622 | 0.02 | SM possible. | | | | | |
| 874.726 | 0.02 | SM{d16:1,23:0}+101.11 | | | | | |
| 896.698 | 0.03 | SM{d16:1,24:1}+101.11 | | | | | |

FIG. 20B

| precursor m/z | precursor intensity [%] | identified SM | | |
|---|---|---|---|---|
| 675.518 | 0.90 | SM(d18:1,14:0) [100%] | | |
| 685.53 | 0.03 | PC head group, but may not be a SM. | | |
| 689.535 | 0.34 | SM(d18:1,15:0) [55%] | SM(d17:1,16:0) [41%] | SM(d19:1,14:0) [5%] |
| 699.522 | 0.02 | SM(d18:1,16:2) [manual] | | |
| 701.534 | 0.54 | SM(d18:2,16:0) [61%] | SM(d18:1,16:1(n-9)) [39%] | |
| 703.518 | 83.47 | SM(d18:1,16:0) [90%] | SM(d19:1,15:0) [10%] | |
| 715.547 | 0.03 | SM, but chains are not identified. | | |
| 717.562 | 0.62 | SM(d18:1,17:0) [85%] | SM(d19:1,16:0) [15%] | |
| 725.531 | 0.01 | SM(d18:1,18:3) [manual] | | |
| 727.55 | 0.20 | SM(d18:1,18:2(n-6,-9)) [100%] | | |
| 729.564 | 0.41 | SM(d18:1,18:1(n-9)) [94%] | SM(d18:2,18:0) [6%] | |
| 731.57 | 5.36 | SM(d18:1,18:0) [94%] | SM(d19:1,17:0) [6%] | |
| 745.593 | 0.12 | SM(d18:1,19:0) [86%] | SM(d19:1,18:0) [14%] | |
| 755.579 | 0.02 | SM(d18:1,20:2) [100%] | | |
| 757.593 | 0.11 | SM(d18:1,20:1(n-9)) [91%] | | |
| 759.606 | 1.06 | SM(d18:1,20:0) [94%] | SM(d19:1,19:0) [6%] | |
| 773.623 | 0.14 | SM(d18:1,21:0) [100%] | | |
| 781.592 | 0.02 | SM(d18:1,22:3) [100%] | | |
| 783.607 | 0.13 | SM(d18:1,22:2(n-6,-9)) [100%] | | |
| 785.62 | 0.29 | SM(d18:1,22:1(n-9)) [93%] | | |
| 787.631 | 1.83 | SM(d18:1,22:0) [94%] | | |
| 799.635 | 0.07 | SM(d18:1,23:1(n-9)) [95%] | | |
| 801.648 | 0.44 | SM(d18:1,23:0) [92%] | SM(d19:1,22:0) [8%] | |
| 804.662 | 0.10 | SM(d18:1,16:0)+101.1 | | |
| 807.613 | 0.06 | SM(d18:1,24:4(n-6,-9,-12,-15)) [100%] | | |
| 809.621 | 0.12 | SM(d18:1,24:3(n-6,-9,-12)) [100%] | | |
| 811.633 | 0.66 | SM(d18:1,24:2(n-6,-9)) [91%] | | |
| 813.643 | 1.85 | SM(d18:1,24:1(n-9)) [94%] | | |
| 829.657 | 0.07 | SM(d18:1,25:0) [95%] | | |

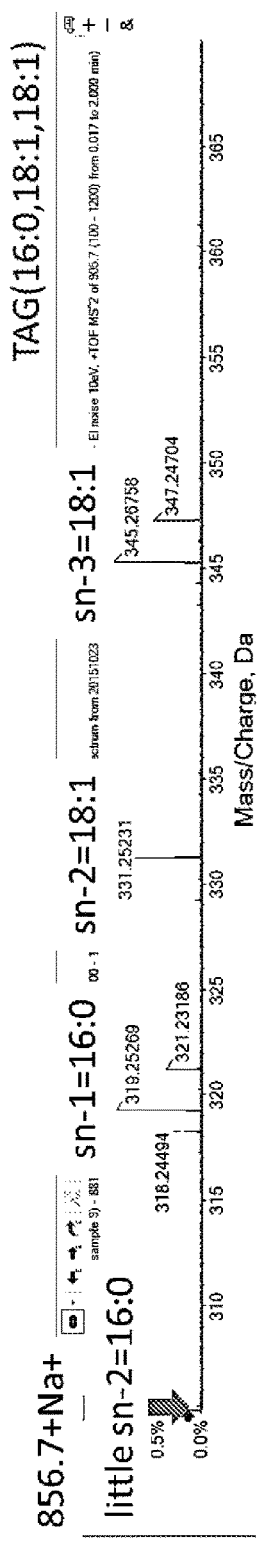
FIG. 24
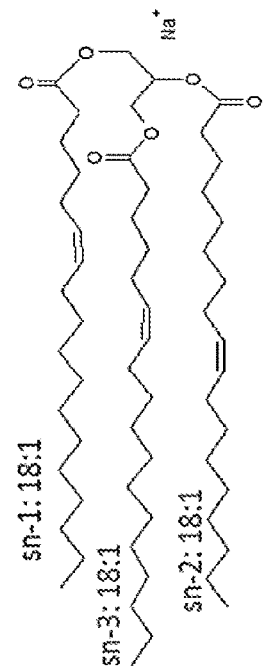
(b) POP
(c) OOO
(a) PPO
FIG. 25

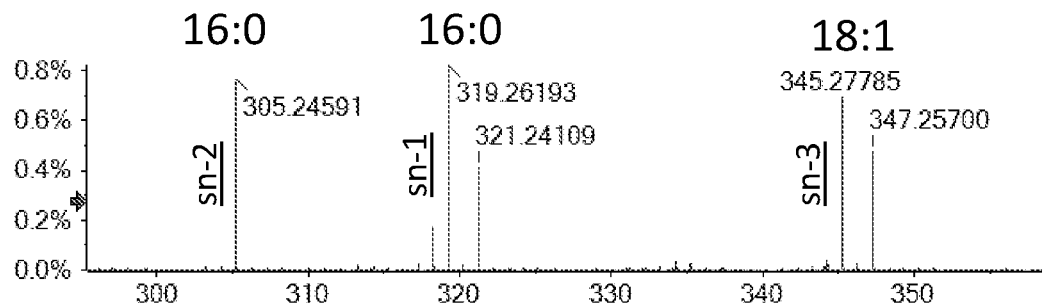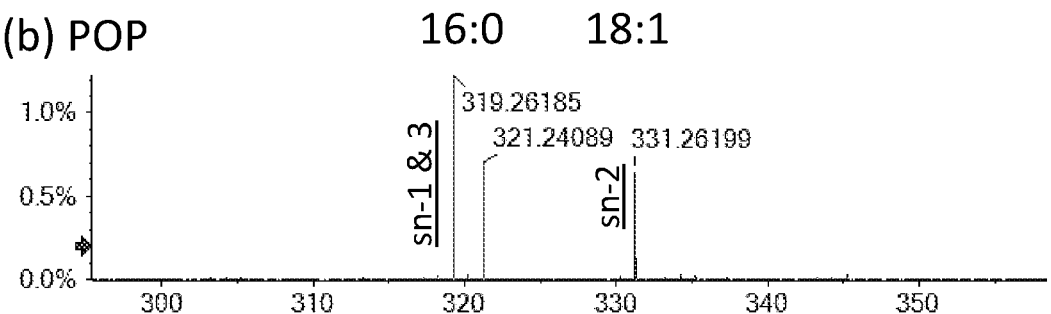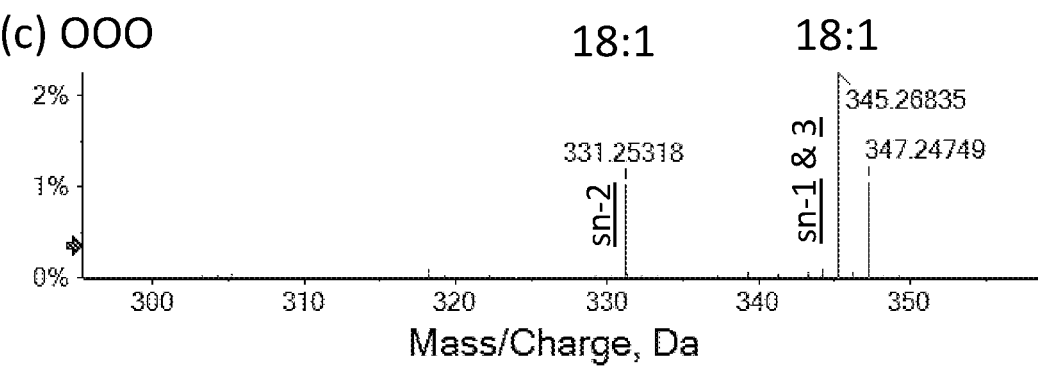
FIG. 27

Greek Olive Oil

| precursor m/z (sodiated) | amount [%] | unsaturated acyl type | | identified TAG (more than 10%) |
|---|---|---|---|---|
| 825.671 | 0.01 | ? | TAG(16:1,16:1,16:0)[100%] | |
| 827.685 | 0.04 | (ω-6)[42%],(ω-7)[58%] | TAG(16:0,16:1,16:0)[100%] | |
| 851.691 | 0.17 | (ω-6)[100%] | TAG(16:0,18:3,16:0)[31%] | TAG(16:1,18:1,16:1)[28%] TAG(16:1,18:2,16:0)[13%] TAG(16:0,16:2,18:1)[13%] |
| 853.703 | 0.98 | (ω-9)[100%] | TAG(16:0,18:2,16:0)[44%] | TAG(16:1,18:1,16:0)[39%] TAG(16:0,16:1,18:1)[17%] |
| 855.722 | 2.67 | (ω-6)[100%] | TAG(16:0,18:1,16:0)[100%] | |
| 865.702 | 0.03 | (ω-6)[100%] | TAG(17:1,16:1,18:1)[44%] | TAG(16:0,18:1,17:2)[40%] TAG(17:1,17:1,17:1)[16%] |
| 867.722 | 0.08 | (ω-9)[100%] | TAG(16:0,18:1,17:1)[52%] | TAG(17:1,17:0,17:1)[48%] |
| 877.705 | 1.11 | (ω-3)[11%],(ω-6)[56%],(ω-9)[33%] | TAG(16:0,18:3,18:1)[23%] | TAG(16:1,18:2,18:1)[22%] TAG(16:0,18:1,18:3)[18%] TAG(16:0,18:2,18:2)[17%] |
| 879.722 | 5.21 | (ω-6)[51%],(ω-9)[49%] | TAG(16:0,18:2,18:1)[34%] | TAG(16:1,18:1,18:1)[32%] TAG(16:0,18:1,18:2)[22%] TAG(18:1,16:1,18:1)[12%] |
| 881.738 | 17.79 | (ω-6)[10%],(ω-9)[90%] | TAG(16:0,18:1,18:1)[100%] | |
| 893.737 | 0.17 | (ω-9)[100%] | TAG(17:1,19:1,17:1)[50%] | TAG(18:1,17:1,18:1)[44%] TAG(17:1,18:1,18:1)[6%] |
| 895.748 | 0.19 | (ω-9)[100%] | TAG(17:0,18:1,18:1)[27%] | TAG(18:1,17:0,18:1)[23%] TAG(17:1,18:0,18:1)[16%] TAG(16:0,20:1,17:1)[12%] |
| 897.735 | 0.13 | (ω-9)[100%] | TAG(16:0,19:0,18:1)[69%] | TAG(17:0,19:1,17:0)[18%] TAG(17:0,18:0,18:1)[13%] |
| 903.723 | 2.02 | (ω-6)[56%],(ω-9)[44%] | TAG(18:1,18:3,18:1)[54%] | TAG(18:2,18:1,18:2)[30%] TAG(18:3,18:1,18:1)[16%] |
| 907.752 | 29.69 | (ω-9)[100%] | TAG(18:1,18:1,18:1)[100%] | |
| 905.736 | 8.10 | (ω-6)[100%] | TAG(18:1,18:2,18:1)[62%] | TAG(18:2,18:1,18:1)[38%] |
| 907.752 | 29.69 | (ω-6)[11%],(ω-9)[89%] | TAG(18:1,18:1,18:1)[100%] | |
| 919.708 | 0.05 | (ω-6)[44%],(ω-9)[56%] | TAG(18:1,19:2,18:1)[61%] | TAG(18:2,19:0,18:2)[22%] TAG(18:2,18:1,19:1)[13%] |
| 921.726 | 0.13 | (ω-9)[100%] | TAG(18:1,19:1,19:1)[54%] | TAG(18:1,19:1,18:1)[46%] |
| 935.785 | 0.50 | (ω-6)[32%],(ω-9)[68%] | TAG(18:1,18:1,20:1)[77%] | TAG(18:2,18:1,20:0)[18%] |
| 937.799 | 0.71 | (ω-3)[16%],(ω-6)[26%],(ω-9)[58%] | TAG(18:1,18:1,20:0)[100%] | |
| 963.806 | 0.31 | (ω-9)[100%] | TAG(18:2,18:1,22:0)[100%] | |
| 965.832 | 0.15 | (ω-9)[100%] | TAG(18:1,18:1,22:0)[100%] | |
| 979.833 | 0.03 | (ω-9)[100%] | TAG(18:1,18:1,23:0)[100%] | |
| 993.85 | 0.05 | ? | TAG(18:1,18:1,24:0)[100%] | |

FIG. 29

ω-3 enriched egg

| precursor m/z [sodiated] | amount [%] | unsaturated acyl type | Identified TAGs | | | |
|---|---|---|---|---|---|---|
| 825.667 | 0.41 | (ω-6)[100%] | TAG[16:1,16:1,16:0][100%] | | | |
| 827.685 | 0.49 | ? | TAG[16:0,16:1,16:0][69%] | TAG[16:1,16:0,16:0][31%] | | |
| 851.683 | 2.60 | (ω-3)[7%],(ω-9)[93%] | TAG[16:1,18:2,16:0][72%] | TAG[16:1,16:1,18:1][15%] | TAG[16:0,18:3,16:0][13%] | |
| 853.703 | 4.37 | (ω-6)[100%] | TAG[16:1,18:1,16:0][43%] | TAG[16:0,18:2,16:0][29%] | TAG[16:0,16:1,18:1][28%] | |
| 855.714 | 3.20 | (ω-9)[100%] | TAG[16:0,18:1,16:0][73%] | TAG[16:0,16:0,18:1][27%] | | |
| 857.727 | 0.70 | ? | TAG[16:0,18:0,16:0][59%] | TAG[16:0,16:0,18:0][41%] | | |
| 865.698 | 0.35 | (ω-6)[71%],(ω-9)[29%] | TAG[16:0,18:2,17:1][73%] | TAG[15:1,18:1,17:1][27%] | | |
| 867.714 | 0.42 | ? | TAG[17:1,17:0,17:1][42%] | TAG[15:0,18:1,18:1][24%] | TAG[16:0,17:1,18:1][23%] | TAG[17:1,17:1,17:0][11%] |
| 873.672 | 1.05 | (ω-3)[65%],(ω-6)[35%] | TAG[16:0,18:3,18:3][46%] | TAG[16:1,18:2,18:3][41%] | | |
| 875.685 | 3.62 | (ω-3)[38%],(ω-6)[42%],(ω-9)[20%] | TAG[16:0,18:2,18:3][52%] | TAG[16:1,18:3,18:1][23%] | TAG[18:2,16:1,18:2][14%] | TAG[16:1,18:2,18:2][10%] |
| 877.701 | 10.59 | (ω-3)[25%],(ω-6)[44%],(ω-9)[31%] | TAG[16:0,18:3,18:1][40%] | TAG[15:1,18:2,18:1][22%] | TAG[16:0,18:2,18:2][21%] | TAG[16:0,18:1,18:3][15%] |
| 879.718 | 21.82 | (ω-6)[59%],(ω-9)[41%] | TAG[16:0,18:2,18:1][87%] | TAG[16:1,18:1,18:1][13%] | | |
| 881.73 | 20.34 | (ω-6)[20%],(ω-9)[80%] | TAG[16:0,18:1,18:1][93%] | TAG[16:0,18:2,18:0][7%] | | |
| 891.708 | 0.30 | (ω-9)[100%] | TAG[18:3,17:0,18:1][70%] | TAG[18:2,17:0,18:2][30%] | | |
| 893.724 | 0.52 | (ω-3)[1%],(ω-6)[51%],(ω-9)[48%] | TAG[17:1,18:1,18:1][30%] | TAG[18:1,17:1,18:1][23%] | TAG[17:0,18:1,18:2][22%] | TAG[17:1,19:1,17:1][15%] |
| 895.739 | 0.46 | (ω-6)[100%] | TAG[17:0,18:1,18:1][71%] | TAG[16:0,19:1,18:1][16%] | TAG[17:0,18:0,18:2][13%] | |
| 899.687 | 1.92 | (ω-3)[54%],(ω-6)[30%],(ω-9)[15%] | TAG[18:3,18:1,18:3][50%] | TAG[18:3,18:2,18:2][24%] | TAG[18:3,18:2,18:2][15%] | TAG[18:2,18:3,18:2][12%] |
| 901.7 | 4.85 | (ω-3)[30%],(ω-6)[47%],(ω-9)[23%] | TAG[18:3,18:2,18:1][70%] | TAG[18:2,18:2,18:2][30%] | | |
| 903.715 | 6.38 | (ω-3)[24%],(ω-6)[36%],(ω-9)[39%] | TAG[18:3,18:1,18:1][56%] | TAG[18:2,18:2,18:1][23%] | TAG[18:1,18:3,18:1][12%] | |
| 905.728 | 6.57 | (ω-3)[5%],(ω-6)[48%],(ω-9)[47%] | TAG[18:1,18:2,18:1][72%] | TAG[18:2,18:1,18:1][28%] | | |
| 907.748 | 5.92 | (ω-6)[30%],(ω-9)[70%] | TAG[18:1,18:1,18:1][81%] | TAG[18:1,18:2,18:0][19%] | | |
| 909.761 | 2.85 | (ω-6)[100%] | TAG[18:1,18:0,18:1][100%] | | | |
| 933.756 | 0.16 | (ω-6)[36%],(ω-9)[64%] | TAG[18:1,20:3,18:0][100%] | | | |

FIG. 30 sn-1, sn-3 diagnostic peak m/z (sodiated)

| | double bond #: 0 | 1 | 2 | 3 | 4 | 5 | 6 |
|---|---|---|---|---|---|---|---|
| length: 12 | 263.199,265.178 | 261.183,263.162 | | | | | |
| 13 | 277.214,279.194 | 275.199,277.178 | | | | | |
| 14 | 291.230,293.209 | 289.214,291.194 | 287.199,289.178 | | | | |
| 15 | 305.246,307.225 | 303.230,305.209 | 301.214,303.194 | | | | |
| 16 | 319.261,321.240 | 317.246,319.225 | 315.230,317.209 | 313.214,315.194 | | | |
| 17 | 333.277,335.256 | 331.261,333.240 | 329.246,331.225 | 327.230,329.209 | | | |
| 18 | 347.293,349.272 | 345.277,347.256 | 343.261,345.240 | 341.246,343.225 | 339.230,341.209 | | |
| 19 | 361.308,363.287 | 359.293,361.272 | 357.277,359.256 | 355.261,357.240 | 353.246,355.225 | | |
| 20 | 375.324,377.303 | 373.308,375.287 | 371.293,373.272 | 369.277,371.256 | 367.261,369.240 | 365.246,367.225 | |
| 21 | 389.339,391.319 | 387.324,389.303 | 385.308,387.287 | 383.293,385.272 | 381.277,383.256 | 379.261,381.240 | |
| 22 | 403.355,405.334 | 401.339,403.319 | 399.324,401.303 | 397.308,399.287 | 395.293,397.272 | 393.277,395.256 | 391.261,393.240 | sn-2 diagnostic peak m/z (sodiated)

| | double bond #: 0 | 1 | 2 | 3 | 4 | 5 | 6 |
|---|---|---|---|---|---|---|---|
| length: 12 | 249.183 | 247.167 | | | | | |
| 13 | 263.199 | 261.183 | | | | | |
| 14 | 277.214 | 275.199 | 273.183 | | | | |
| 15 | 291.23 | 289.214 | 287.199 | | | | |
| 16 | 305.246 | 303.23 | 301.214 | 299.199 | | | |
| 17 | 319.261 | 317.246 | 315.23 | 313.214 | | | |
| 18 | 333.277 | 331.261 | 329.246 | 327.23 | 325.214 | | |
| 19 | 347.293 | 345.277 | 343.261 | 341.246 | 339.23 | | |
| 20 | 361.308 | 359.293 | 357.277 | 355.261 | 353.246 | 351.23 | |
| 21 | 375.324 | 373.308 | 371.293 | 369.277 | 367.261 | 365.246 | |
| 22 | 389.339 | 387.324 | 385.308 | 383.293 | 381.277 | 379.261 | 377.246 |

FIG. 31

METHOD AND APPARATUS FOR ANALYZING SAMPLES USING MASS SPECTROMETRY

RELATED US APPLICATIONS

This application claims the benefit of priority from U.S. Provisional Application Ser. No. 62/268,912, filed on Dec. 17, 2015 and U.S. Provisional Application Ser. No. 62/329,679, filed on Apr. 29, 2016, the entire contents of both of which are hereby incorporated by reference herein.

FIELD

The invention generally relates to mass spectrometry, and more particularly to methods and apparatus for the analysis of lipids involving the detection of isomeric lipids and/or the location and/or identification of double bonds within a lipid molecule.

INTRODUCTION

Mass spectrometry (MS) is an important tool for the quantification and structural analysis of organic compounds. Advanced techniques have been developed to analyze larger and more complex molecules by dissociating molecules into smaller fragments within a mass spectrometer or a tandem spectrometer (MS/MS) prior to detection. Analysis of the fragments may provide detailed structural information unavailable through examination of the intact ionized molecules. Various techniques have been developed for inducing dissociation. One early example is collision induced dissociation (CID) in which sample ions are accelerated into gas atoms or molecules to induce fragmentation. Another example is electron capture dissociation (ECD) in which sample ions interact with electrons having a kinetic energy of about 0 electron Volts (eV) to about 3 eV (also referred to as "hot" ECD (HECD) for electrons having a kinetic energy above about 5 eV to about 10 eV). In ECD, multiply charged sample ions are fragmented as the sample ion captures an electron and charge neutralization occurs at the capture site, leading to an excited radical species that undergoes bond cleavage. A similar electron-based technique, referred to as electron induced dissociation (EID) or electron impact (EI) excitation of ions from organics (EIEIO), can be employed to analyze smaller singly charged sample ions by increasing the electron kinetic energy above 3 eV. Other reported dissociation techniques include electron transfer dissociation (ETD) (using reagent anions) and electron detachment dissociation (EDD) (using electrons with kinetic energy of greater than 3 eV to dissociate negatively charged sample ions). Proton transfer reactions (PTR) can also be utilized to reduce the charge state of ions in which a proton is transferred from one charged species to another.

WO2014/191821, herein incorporated by reference in its entirety disclosed an apparatus and method of operation for performing, amongst other things, an electron-ion reaction, such as ECD. These devices can be utilized to perform, for example, EID, EIEIO, or EDD.

Dissociation techniques have proven to be very useful for MS analysis of organic compounds, including bio-molecular species such as peptides, proteins, glycans, and post translationally modified peptides/proteins. However, substantial limitations remain for MS analysis of certain types of molecular samples and structural details thereof. For example, traditional mass spectrometry techniques are sometimes inadequate to discriminate between two or more isomeric species in a sample. Such information is often significant because, despite the structural similarity of isomeric species, their biological activity can vary drastically. Moreover, the presence of a particular isomer and/or the relative abundance of the isomers can be important for medical diagnostics. For example, certain lipid molecules can exist as regioisomers that contain the same core structure and side chains, although the side chains can be arranged in more than one position. Certain regioisomers can serve as critical biomarkers for disease and/or provide information regarding underlying biomolecular activity based, for instance, on the relative abundance of the various regioisomers in tissues (i.e., brain vs. kidney). However, conventional MS- and MS/MS-based techniques have not been able to generate mass spectra with adequate information and easily interpretable spectra to allow for resolution of the isomeric species for many regioisomeric samples.

An illustrative regioisomer sample involves the two most common phosphatidylcholine (PC) regioisomers 1-palmatoyl-2-oleoyl-sn-phosphatidylcholine (POPC) and 1-oleoyl-2-palmatoyl-sn-phosphatidylcholine (OPPC). Other specific illustrative regioisomer samples includes the triacylglycerol (TAG) compounds 1,2-dipalmitoyl-3-oleoyl-rac-glycerol (PPO) and 1,3-dipalmitoyl-2-oleoyl glycerol (POP). Another related compound though not a regioisomer is trioleyolyglycerol (OOO).

Although both positive-mode and negative-modes of MS/MS have shown some promise in individually quantifying POPC and OPPC based on the diagnostic fragment ions present in their MS/MS fragmentation spectra, it nonetheless remains difficult to quantify a particular species in a mixture containing both isomers as their fragmentation behavior is essentially identical. Further, no chromatographic separation is presently available. Indeed, when OPPC and POPC are both present, their MS/MS fragmentation spectra are convolved such that these lipid regioisomers are generally analyzed and quantified in tandem (i.e., without enumerating the abundance of each particular isomer) or with low-resolution assessments of the relative ratio of the two regioisomers made available by MS/MS of the negatively charged forms of these PCs. Similarly, many other isomeric lipids, including but not limited to triacylglycerols (TAGs) and diacylglycerols (DGs), are difficult to quantify individually when present in a mixture.

Other illustrative lipid samples are the sphingomyelin (SM) type lipids in the class of sphingolipids. SMs are similar to PCs since they also contain phosphocholine as their polar head group. However, discrimination of SMs and PCs are made challenging by the fact that both species, when analyzed by positive-mode MS/MS (most sensitive mode of operation for their detection), provide little structural detail other than the presence of the phosphocholine headgroup (i.e., only a fragment ion of m/z 184 appears in the MS/MS spectra).

In another example, MS and/or MS/MS techniques are able to generate spectra that allow for the determination of class, carbon chain length, and degree of unsaturation (i.e., double bonds) and double bond orientation of some lipids. However, determination of the actual carbon-carbon double bond position within a sample molecule has remained elusive. The number and location of double bonds can have a significant bearing on understanding the chemical reactivity or biological importance of a molecule. One technique for identifying the number and location of double bonds in a molecule using MS is ozone-induced dissociation (OzID), which involves the reaction of ozone with a sample molecule to cleave carbon-carbon double bonds in a specific, characteristic manner. OzID requires the generation of a stable pressure of ozone—a toxic gas—that necessitates additional gas generation hardware and ion-trapping capabilities to permit a reasonable ion/molecule reaction period for OzID to occur. High-energy CID has been employed to determine double-bond location within a lipid molecule. However, CID is difficult to employ practically because the technique is not able to efficiently generate diagnostic fragment ions. In addition, bond fragmentation is quite extensive, providing a difficult challenge to discern the presence of double-bond location characteristic fragment ions, especially from a mixture of isomeric species. As such, there is insufficient confidence in the determination of double-bond position from resultant spectra to make the analysis analytically useful.

WO2015/189749 and Anal. Chem. 2015, 87, pp. 5837-5845, both herein incorporated by reference, disclosed MS-based methods of identifying a lipid's head group, the length of acyl chains, the presence of double bonds in the acyl chains including their regioisomerism (e.g., identification of acyl chains at sn-1 and sn-2) using novel electron-based dissociation methods. These methods, however, did not describe a method of identifying the cis or trans orientation of any of the detected carbon-carbon double bonds.

Accordingly, there remains a need for improved quantitation of isomeric lipids with enhanced discrimination between species and/or the ability to easily and confidently determine the position of double bonds and/or their cis/trans orientation in an efficient MS or MS/MS work flow.

SUMMARY

Apparati, systems, and methods in accordance with the applicants' present teachings allow for the analysis of lipids in an analytical sample using mass spectrometry, including determining isomeric species within a mixture of lipids and the locations of double bonds and their orientation within a lipid molecule. Ionized lipid molecules in an analytical sample may be subjected to a dissociation reaction by reacting the ionized lipid molecules with electrons (i.e., an electron beam) within a reaction device of a mass spectrometer to form various fragments of the lipid molecules. The electrons may have a kinetic energy of about 1 electron Volts (eV) to about 12 eV. The fragments may be detected by a detector of the mass spectrometer to generate spectra for the analytical sample. The fragments generated by the dissociation reaction according to applicants' present teachings are conducive to, among other things, discerning lipid isomers in an analytical sample including a mixture of isomers and determining locations of double bonds of lipid molecules in the analytical sample and/or the cis/trans orientation of the double bonds.

These and other features of the applicants' teachings are set forth herein.

In accordance with various aspects and certain embodiments, the present teachings relate to a method for analyzing a sample. The sample may contain at least one carbon-carbon double bond containing lipid and may be analyzed using a mass spectrometer. The method can comprise: ionizing the sample to form a plurality of precursor ions, fragmenting at least a portion of the plurality of precursor ions into a plurality of fragment ions by irradiating the plurality of precursors ions with electrons; wherein the dissociation reaction is configured to allow distinguishing mass signatures of two isomeric species of said at least one carbon-carbon double-bond containing lipid; and detecting at least a portion of the plurality of fragment ions at a detector of the mass spectrometer to form at least one spectrum for mass analysis of the sample, and wherein peak intensities associated with the plurality of fragment ions in said at least one spectrum is used to indicate the cis/trans orientation of said at least one carbon-carbon double bond. In some aspects, the electrons have a kinetic energy of about 4 electron volts to about 12 electron volts.

In some aspects, the peak intensities associated with the plurality of fragment ions are characteristic of a carbon-carbon single bond situated next to said carbon-carbon double-bond. In some aspects, the carbon-carbon single bond is situated at a position +1 to the location of the carbon-carbon double bond along a carbon chain of said lipid.

In some aspects, the peak intensities associated with the plurality of fragment ions comprise a first peak characteristic of non-radical species and a second peak characteristic of a radical fragment species. In some aspects, the first peak and said second peak are separated by about 1 Dalton in the spectrum.

In some aspects, a ratio of the first peak to the second peak is determined and the ratio is used to indicate the cis/trans orientation of the at least one carbon-carbon double bond. In some aspects, the ratio is compared to a standard ratio, wherein the standard ratio is obtained by analyzing a standard sample utilizing the same method utilized to calculate the ratio with the exception that the standard sample comprises a lipid species that consists essentially of either a pure cis or pure trans form of said double-bond containing lipid. In some aspects, a relative abundance of cis and trans double bonds present in the sample is determined based on the ratio and the standard ratio.

In some aspects in accordance with the teachings provided herein, the plurality of precursor ions are single-charged species.

In accordance with various aspects of the present teachings, a method for analyzing a sample containing or suspected of containing at least one carbon-carbon double-bond-containing lipid using a mass spectrometer is disclosed. The method comprising ionizing the sample to form a plurality of singly-charged precursor ion species; performing an ion-electron reaction to fragment at least a portion of the plurality of precursor ion species into a plurality of product ion species, the ion-electron reaction comprising irradiating the plurality of precursor ions with electrons having a kinetic energy of about 4 electron volts to about 12 electron volts; and detecting at least a portion of the plurality of product ion species at a detector of the mass spectrometer to form at least one spectrum for mass analysis of the sample, and wherein peak intensities associated with the plurality of product ions indicates the cis/trans orientation of said at least one carbon-carbon double bond.

In accordance with various aspects of the present teachings, a method for analyzing a sample containing or suspected of containing at least one carbon-carbon double-bond-containing lipid using a mass spectrometer is described. The method comprising ionizing the sample to form a plurality of singly-charged precursor ion species; performing an ion-electron reaction to fragment at least a portion of the plurality of precursor ion species into a plurality of product ion species, the ion-electron reaction comprising irradiating the plurality of precursor ions with electrons having a kinetic energy of about 4 electron volts to about 12 electron volts; and detecting at least a portion of the plurality of product ion species at a detector of the mass spectrometer to form at least one spectrum for mass analysis of the sample, and associating a first peak on said spectrum with a radical species and associating a second peak on said spectrum with a non-radical fragment species, the first and second peaks corresponding to a carbon-carbon single bond that is positioned next to said carbon-carbon double bond, and determining the relative abundance of cis and trans double bonds present in said species from the ratios of the intensities of the radical species and the hydrogen loss species.

In accordance with various aspects of the present teachings, a system for analyzing a sample containing a carbon-carbon double-bond-containing lipid is disclosed. The system comprising: a mass spectrometer comprising an ion-electron reaction device and a mass analyzer; a processor in communication with the mass spectrometer configured to: instruct the ion-election reaction device to conduct an ion-electron reaction between an ionized lipid containing a carbon-carbon double bond and electrons that causes the production of two or more product ions; receive an intensity for each of the two or more product ions from the mass spectrometer; identifies a grouping of the two or more product ions and their associated intensities that is characteristic of a carbon-carbon single bond situated next to said carbon-carbon double bond, at least one or the two or more product ions being characteristic of a non-radical species and another of the two or more product ions being characteristic of a radical species; determines a ratio of the intensities of said non-radical species to the radical species; and determines the cis/trans orientation of the carbon-carbon double bond based on the ratio.

In various aspects, the processor identifies a grouping of two or more product ions and their associated intensities that is characteristic of a carbon-carbon double bond, at least one of these characteristic double-bond intensities corresponding to a double-bond radical fragment.

In various aspects, the double-bond radical fragment and the radical species are separated by 12 Daltons. In various aspects, the ionized lipid is singly charged.

In various aspects, a method for analyzing a sample containing or suspected of containing at least one lipid using a mass spectrometer, the lipid being selected from the group of sphingomyelins, is disclosed. The method comprising: ionizing the sample to form a plurality of precursor ions; performing an electron-ion reaction to fragment at least a portion of the plurality of precursor ions into a plurality of product ions, detecting at least a portion of the plurality of product ion species at a detector of the mass spectrometer to form at least one spectrum for mass analysis of the sample and determining the presence of at least one sphingomyelin species in said sample by identifying in said spectrum, diagnostic peaks situated at about m/z 184.075 and about m/z 225.100 or at about m/z 184.075, about m/z 225.100 and about m/z 253.095. In various aspect, a DMS separation is performed between the steps of ionizing of the sample and the electron-ion reaction.

In various aspects, a method for analyzing a sample containing or suspected of containing at least one lipid using a mass spectrometer is disclosed. The lipid being selected from the group of triacylglycerols and where the method comprises: ionizing the sample to form a plurality of precursor ions; performing an electron-ion reaction to fragment at least a portion of the plurality of precursor ions into a plurality of product ions, detecting at least a portion of the plurality of product ion species at a detector of the mass spectrometer to form at least one spectrum for mass analysis of the sample; and wherein the lipid is complexed with an alkali metal salt prior to ionization. In various aspects, the lipid is complexed with an alkali metal salt in a solution of dichloromethane and methanol. In various aspects, the dichloromethane and methanol are mixed in a 50:50 solution by volume. In various aspects, the alkali metal salt is a sodium salt. In various aspects, the alkali metal salt is sodium acetate.

BRIEF DESCRIPTION OF THE DRAWINGS

The skilled person in the art will understand that the drawings, described below, are for illustration purposes only. The drawings are not intended to limit the scope of the applicants' teachings in any way.

FIG. 2A-D depicts a series of plots (a-n) of the intensity ratio of non-radical (a-m) and hydrogen gain (n) at each carbon-carbon single bond in PC(16:1(9),16:1(9)) as a function of electron energy.

FIG. 18 depicts an MS spectrum of porcine brain SM and a series of identified SM molecules.

FIG. 19 depicts an MS spectrum of BHE and a series of identified SM molecules.

FIG. 24 depicts an analysis of a mixed molecular species of TAG in edible oil.

FIG. 25 depicts a series of TAG structures.

FIG. 27 depicts regioisomerism identification of acyl groups in various TAG structures.

FIG. 29 depicts a series of identified TAG compounds found in a sample of olive oil.

FIG. 30 depicts a series of identified TAG compounds found in a sample of omega-3 enriched chicken egg.

FIG. 31 depicts a list of diagnostic peaks for use in identifying TAG species analyzed by EIEIO.

DETAILED DESCRIPTION

It will be appreciated that for clarity, the following discussion will explicate various aspects of embodiments of the applicants' teachings, while omitting certain specific details wherever convenient or appropriate to do so. For example, discussion of like or analogous features in alternative embodiments may be somewhat abbreviated. Well-known ideas or concepts may also for brevity not be discussed in any great detail. The skilled person will recognize that some embodiments of the applicants' teachings may not require certain of the specifically described details in every implementation, which are set forth herein only to provide a thorough understanding of the embodiments. Similarly it will be apparent that the described embodiments may be susceptible to alteration or variation according to common general knowledge without departing from the scope of the disclosure. The following detailed description of embodiments is not to be regarded as limiting the scope of the applicants' teachings in any manner.

With specific reference to mass units and the location of diagnostic peaks in a mass spectrum, it should be understood that the use of the term "about" in the present teachings when referencing the m/z value should be interpreted to be a reference to the use in a high resolution mass spectrometer and that this should include a range that encompasses ±0.1 Da units. For example, a reference to an m/z value of about 150.01 should be understood to include a mass range of 149.91 to 150.11.

Methods and systems for dissociating lipid ions ("precursor ions") of an analytical sample into fragments ("fragment ions") and analyzing the fragments are provided herein. In accordance with various aspects of the applicants' teachings, the methods and systems can provide for the fragmenting of lipid ions of an analytical sample into fragment ions that may be expressed on an MS spectrum that allows for a detailed determination of the chemical structure of the precursor ions, which may be difficult to achieve with conventional MS techniques. In various aspects, methods and systems in accordance with applicants' teachings can enable a mass spectrometer to resolve a sample's isomeric lipids, such as POPC and OPPC, and/or POP/PPO and/or the location of double bonds of lipid molecules and their cis/trans orientation within a sample, all by way of non-limiting example.

Figure 1:
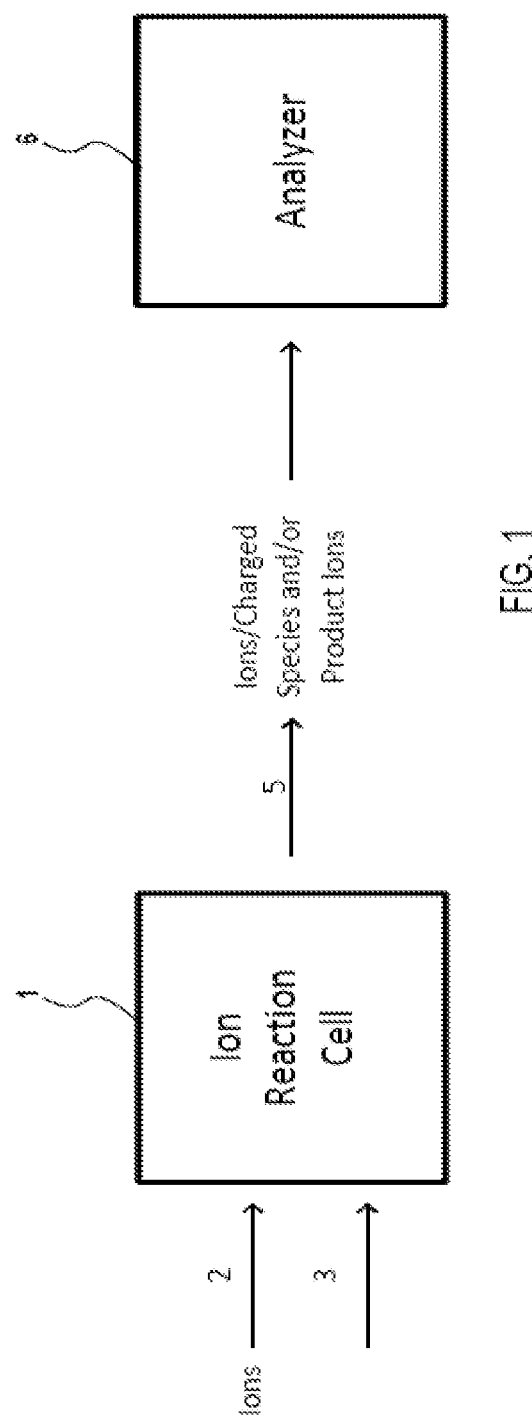
FIG. 1 depicts a schematic view of an implementation of an embodiment of the invention.
Figure 2A:
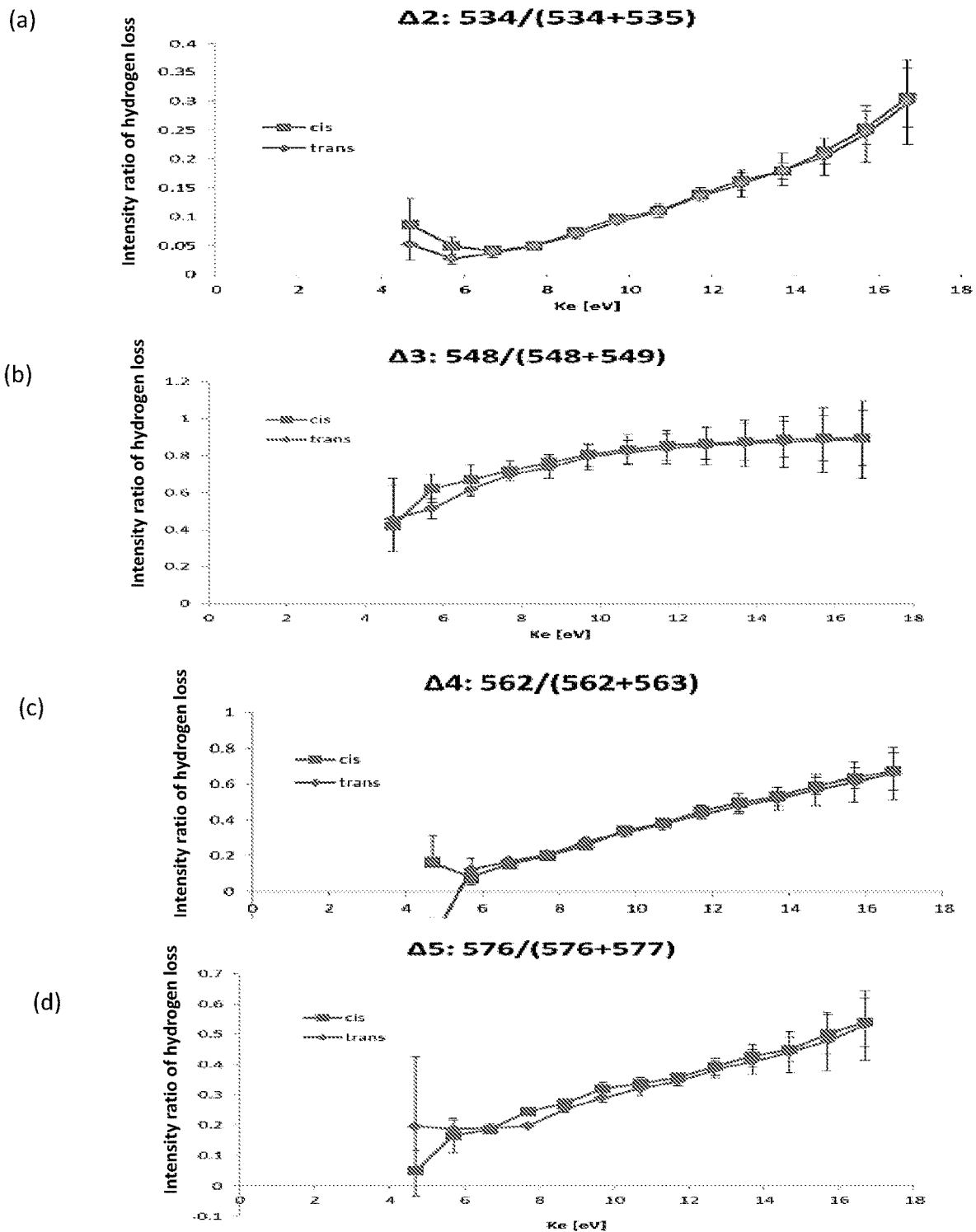
Figure 2B:
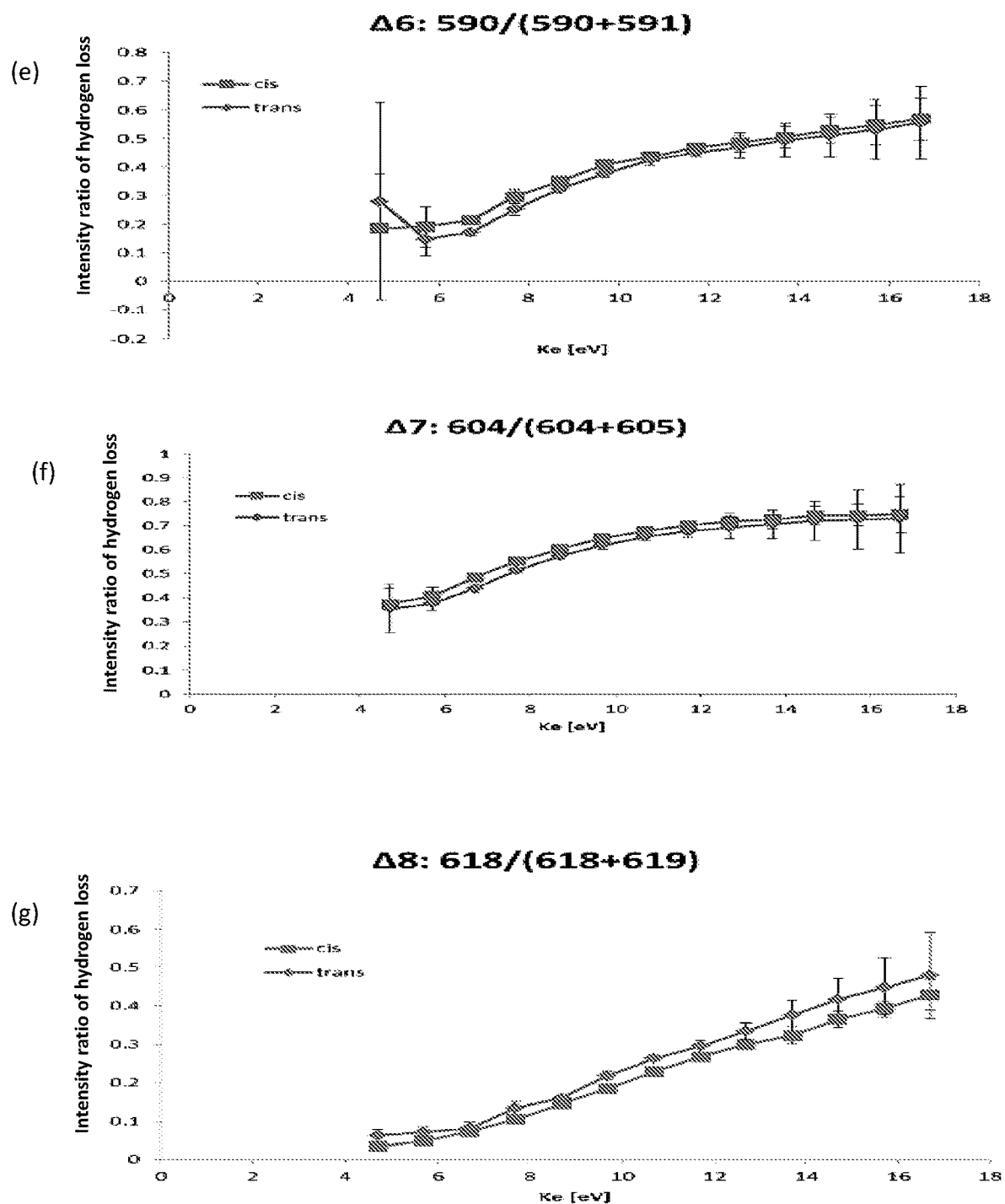

Referring to FIG. 1 there is depicted a general schematic diagram of an ion reaction cell configured to perform various aspects of some embodiments. As discussed below, the ion reaction cell can be incorporated within a mass spectrometer in accordance with the present teachings. As shown in FIG. 1, an ion reaction cell 1 may have as inputs a series of reactants including ions 2 and a charged species 3. The ions 2 can be any ion that is positively (cations) or negatively (anions) charged. A variety of different types of sources for the ions 2 may be employed. Some examples of suitable ion sources include, without limitation, an electrospray ionization (ESI) source, a desorption electrospray ionization (DESI) source, or a sonic spray ionization (SSI) source, an atmospheric pressure chemical ionization (APCI) source, a matrix-assisted laser desorption/ionization (MALDI) source, and a chemical ionization (CI) source, among others. In some embodiments, the ions 2 may be mass selected before being injected into the ion reaction cell 1, for example, using a quadrupole mass selection device.

The charged species 3 can be electrons or ions that are either positively or negatively charged. When the charged species are electrons, the electron source can be a filament such as a tungsten or thoriated tungsten filament or other electron source such as a $Y_2O_3$ cathode. The reaction device can be filled with a cooling gas, for example, such as helium (He) or nitrogen ($N_2$). The typical pressure of the cooling gas can be between $10^{-2}$ to $10^{-4}$ Torr.

Inside the ion reaction cell 1, the ions 2 and the charged species 3 interact. Depending on the nature of reactants utilized, the interaction can cause a number of phenomena to occur which result in the formation of product ions (fragment ions) 5. The product ions 5 can then be extracted or ejected from the ion reaction cell 1 together with potentially other unreacted ions 2 and/or possibly charged species 3 as the circumstances dictate. The extracted product ions 5 can be guided to a mass analyzer 6. The mass analyzer 6 can include a variety of elements including a detector for detecting the ions and generating information for obtaining a mass spectrum of the product ions 5. A variety of mass analyzers known in the art can be employed. An example of a suitable mass analyzer is a quadrupole time-of-flight mass spectrometer, a quadrupole mass spectrometer, an Orbitrap mass spectrometer, and electrostatic trap mass spectrometer, or another tandem configuration thereof.

In accordance with various aspects of the applicants' teachings, the exemplary system discussed above with reference to FIG. 1 can be used to analyze one or more ionized isomeric lipids contained within a sample. In accordance with certain aspects of the present teachings, a lipid molecule (M) contained within a sample can be ionized, for example, by reacting the lipid molecule with a cationization agent ($X^+$) so as to form a cationized lipid molecule ([M+X]$^+$). By way of example, the lipid molecule can be protonated so as to form a protonated lipid molecule ([M+H]$^+$). Cationized lipid molecules can alternatively be formed by associating the lipid molecules with a metal ion such as sodium, potassium, silver, or lithium so as to generate a cationized lipid-metal ion adduct such as [M+Na]$^+$, [M+K]$^+$, [M+Ag]$^+$, and [M+Li]$^+$, respectively, all by way of non-limiting example. In accordance with certain aspects of the present teachings, a lipid molecule (M) contained within a sample can be ionized, for example, by deprotonating techniques so as to form an anionized lipid molecule ([M+H]$^-$). Accordingly, in some embodiments, the ions 2 may include cations. In some embodiments, the ions 2 may include anions. In some embodiments, the ions 2 may include singly-charged ions. In other embodiments, the ions 2 may be multiply charged, such as doubly charged.

In some embodiments, the ions 2 may include cations and the charged species 3 are electrons. Accordingly, the cations may capture the electrons and undergo electron dissociation in which the interaction between ions 2 and charged species 3 results in the formation of product ions (fragment ions) 5 which are fragments of the original ions 2. In some embodiments, the ions 2 may include anions and the charged species 3 are electrons. The anions may capture the electrons and undergo electron dissociation in which the interaction between ions 2 and charged species 3 results in the formation of product ions (fragment ions) 5 which are fragments of the original ions 2. The stream of species ejected from the ion reaction cell may include one or more or a mixture of the ions 2 or the product ions 5 or in some cases, the charged species 3.

In some embodiments, the ion-electron reaction in the ion reaction cell 1 may include electron capture dissociation (ECD), hot electron capture dissociation (HECD), electron transfer dissociation (ETD), electron ionization dissociation (EID), electron-induced excitation of ions in organics (EIEIO), and electron detachment dissociation (EDD). In some embodiments, EIEIO may be used in which electron impact can induce electrical and vibrational excitation of the internal state of molecules resulting in dissociation. In addition, in EIEIO, electrons are not captured by the precursor ions 2 and, as such, EIEIO may be applied to singly-charged molecules. Alternatively, ECD may be applied only to multiply charged precursor ions. However, in accordance with applicants' teachings, EID and EIEIO may be applied to the singly-charged precursor ions generated from the samples.

In some embodiments, the ion reaction cell 1 may be configured as a Fourier transform ion cyclotron resonance cell, a digital Paul trap, a linear ion trap, an electrostatic ion trap, a Chimera trap, or any other type of device or trap configured to facilitate ion-charged species interactions. As an illustrative non-limiting example, devices such as those disclosed in WO2014/191821 (eg. a chimera trap) can be used in accordance with the present teachings.

In some embodiments, the charged species 3 are electrons. In various aspects, the electrons may have a kinetic energy of about 3 eV, about 4 eV, about 5 eV, about 6 eV, about 7 eV, about 8 eV, about 9 eV, about 10 eV, about 11 eV, about 12, eV, about 13 eV, about 14 eV, about 15 eV, about 16 eV, about 17 eV, about 18 eV, about 19 eV, about 20 eV, and any value or range between any two of these values (including endpoints). In various aspects, the electrons may have a kinetic energy of about 4 eV to about 12 eV. In some aspects, the electrons may have a kinetic energy of about 5 eV to about 10 eV. In some aspects, electrons may have lower kinetic energies if the species being exposed to the electrons is doubly charged.

According to various aspects of applicants' teachings, the kinetic energy of the electrons used to dissociate the precursor ions into fragments was about 4 eV to about 12 eV. Preferably, the kinetic energy of the electrons used to dissociate the precursor ions into fragments was about 5 eV to about 10 eV. For certain types of lipid molecules, EID or EIEIO using electrons having a kinetic energy of about 4 eV to about 12 eV generated fragments conducive to determining structural details thereof, including double-bond locations. If the kinetic energy of the electrons was less than about 3 eV, insufficient dissociation was observed for singly charged species. If the kinetic energy of the electrons was greater than about 12 eV, the increase in dissociation and the resulting fragments lead to spectra that were insufficient signal-to-noise to be identified with confidence. Low energy electrons may be appropriate for doubly charged species.

Surprisingly, and as described in more detail below, the use of electron dissociation using electrons with a kinetic energy of about 4 eV to about 12 eV, and particularly about 5 eV to about 10 eV, may fragment lipid molecules to allow for the determination of isomeric species and/or double bond locations and/or their cis/trans orientation within the molecules in accordance with the teachings herein.

It has been found that the cis and trans isomers of a lipid containing a carbon-carbon double bond show differences in a mass spectra after performing an ion-electron reaction (such as EIEIO) at specific electron energies and that these differences can be utilized to differentiate between the two isomers.

Specifically, after locating a grouping of mass spectra peaks associated with a double bond in accordance with the teachings provided in WO 2015/189749, by looking at the groupings of mass spectra peaks that is characteristic of the carbon-carbon bond disposed directly beside the double bond and viewing the non-radical fragment peak, it is possible to infer the orientation of the carbon-carbon double bond by reference to various control samples. The grouping of fragment peaks when measured in a high resolution mass spectrometer will generally comprise a series of at least two peaks, one of which is associated with a radical fragment, one associated with a non-radical fragment resulting from hydrogen atom loss from the aforementioned radical fragment. There may also be additional peaks associated with isotopes of these at least two peaks separated by one or more Da depending on the isotopes present. The non-radical fragment peak is separated from the radical fragment peak by the mass of one hydrogen atom or about 1 Da. Preferably, the grouping of fragment peaks occurring at the carbon-carbon single bond adjacent to the carbon-carbon double bond of interest is located on the terminal side of the fatty acid chain of the lipid molecule being analyzed.

The ratios of intensity of the non-radical fragment peak to the radical fragment peak will differ depending on whether the carbon-carbon double bond is in either a cis or trans isomer. It is believed that this difference in peak intensity ratios is caused by secondary reaction products from the radical fragment that involves hydrogen loss and this hydrogen loss differs significantly between the cis and trans isomers.

While it is conceived that there are numerous methods of utilizing this information to identify the presence of a cis or trans orientation of a double bond, one particular non-limiting example is exemplified herein to determine the ratio of isomers in a mixture that involves the normalization of peak intensities.

A normalized peak difference can be calculated for the grouping of peaks according to Formula 1:

$$\text{Normalized Peak Difference} = \frac{[\text{Intensity of non-radical fragment}] - [\text{Intensity of radical fragment}]}{[\text{Intensity of non-radical fragment}] + [\text{Intensity of radical fragment}]} \quad (1)$$

By obtaining a series of spectra obtained using various electron kinetic energy values and plotting the normalized peak difference as a function of the electron kinetic energies, optimal values for electron kinetic energies can be determined for each double-bond position isomer (e.g., double bond at n–9 position vs. n–6 position) that can be used to differentiate the cis and trans isomers.

As a non-limiting example, this can be demonstrated with reference to FIG. 2A-D which shows various plots (a-m) of the intensity ratios of the non-radical products associated with each of the carbon-carbon single bonds in PC (16:1 (9),16:1(9)) as a function of electron energy. As is evident, only the non-radical product intensity at the Δ10 position (i.e., at the position adjacent to the double bond on the acyl chain terminal side (plot h)) shows significant difference between the cis and trans isomers. Plot n shows a corresponding intensity ratio of the non-radical fragment associated with the 48 position (i.e., located at the position adjacent to the carbon-carbon double bond on the acyl chain head group side). The square traces are indicative of the cis (Z) isomers and the diamond traces indicative of the trans (E) isomers.

Figure 3:
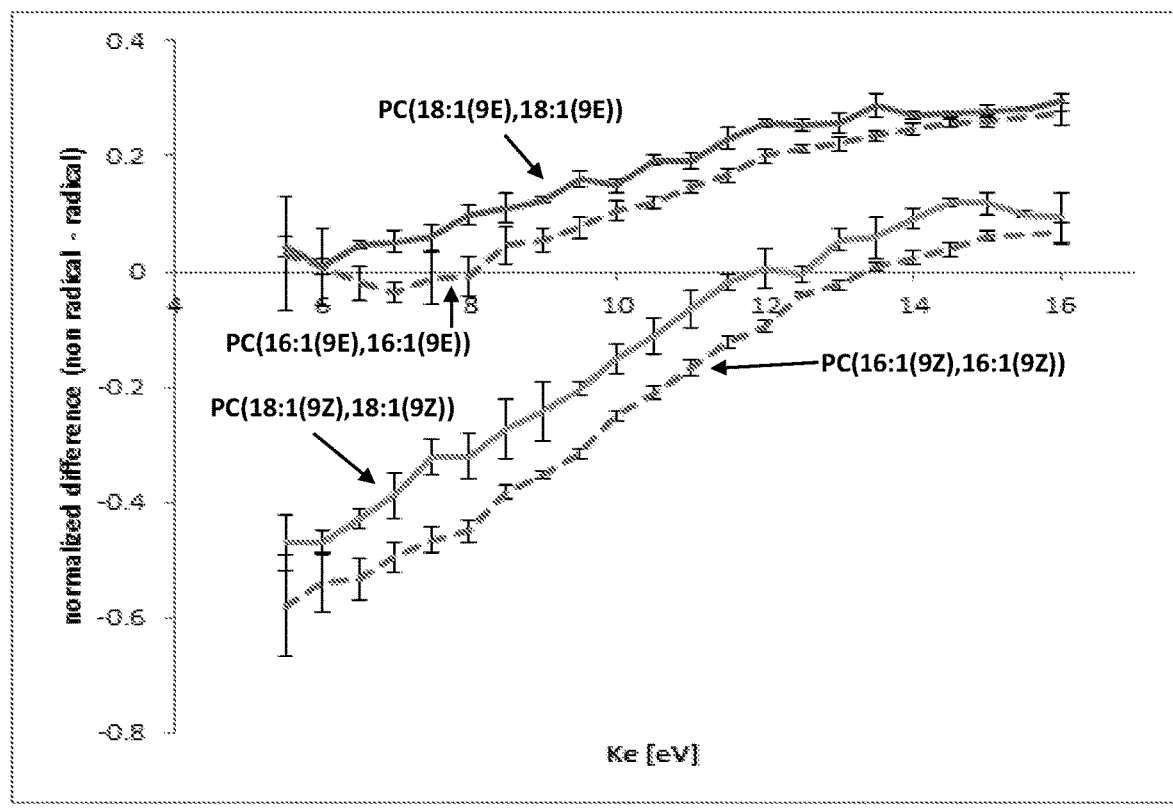
FIG. 3 depicts normalized differences between non-radical and radical peak intensities of different lengths of acyl chains.

FIG. 3 depicts a plot of normalized differences as a function of length of the acyl chains and that such differences between the cis and trans isomers are typically present in chains of varying lengths.

For the analysis of cis-POPC and trans-POPC mixtures, it may be preferable to perform an additional separation step prior to performing the ion-electron reaction. This may involve liquid or gas chromatography or capillary electrophoresis separation. For other types of lipids, separation may be performed by use of an ion mobility spectrometer and more specifically a differential mobility spectrometer (DMS) which may be used for lipid class separation. An illustrative example of a DMS devices that can perform such separations is herein described.

Figure 4:
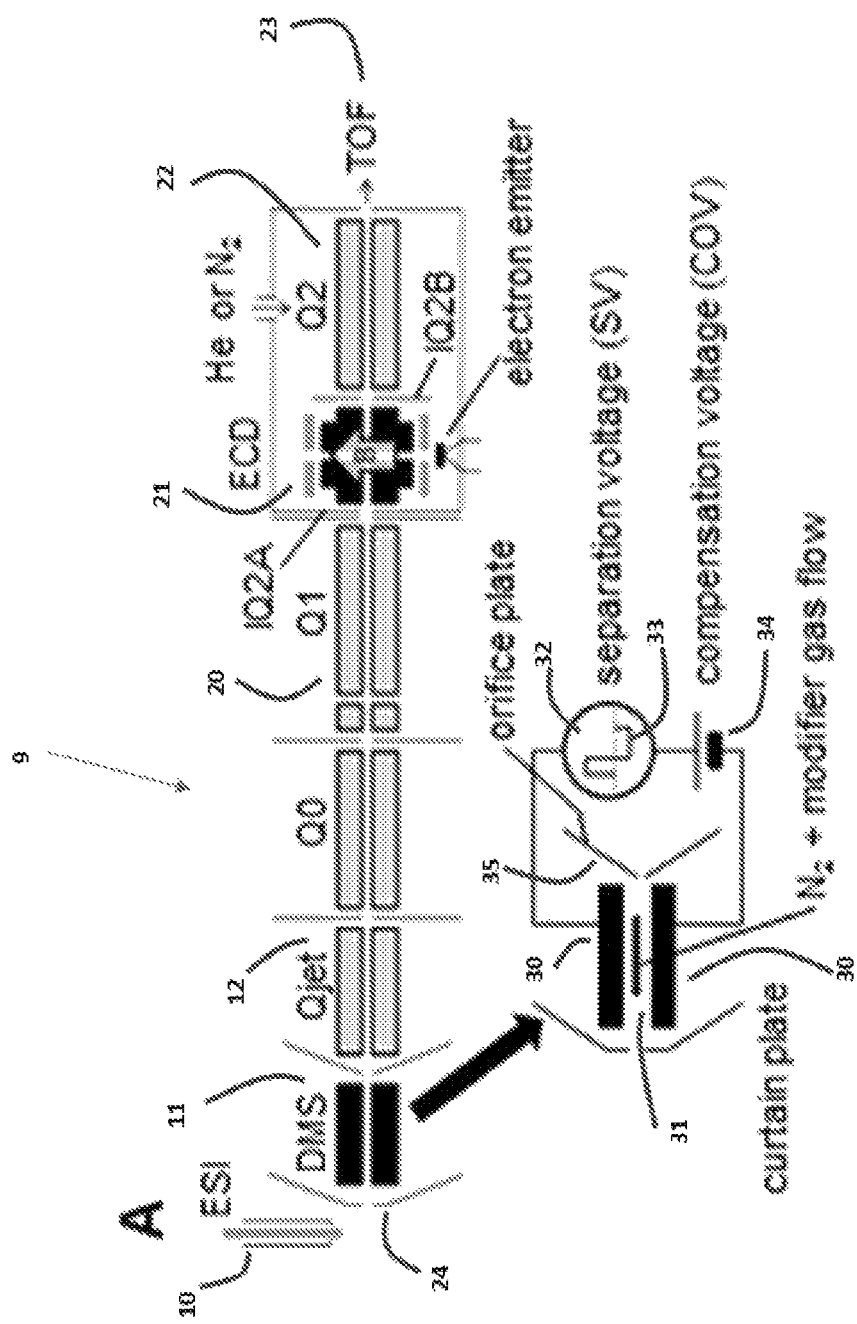
FIG. 4 depicts a simplified side view of an implementation of an embodiment of the invention.

DMS separation may be useful in the analysis of other classes of lipids using the present teachings. Specifically, the class of sphingolipids, including, but not limited to the sphingomyelins, ceramides and glycol-ceramides can be analyzed in a preferential manner utilizing DMS consistent with the present teachings. A non-limiting exemplary DMS containing apparatus 9 in accordance with the present teachings is depicted in FIG. 4. Here, an analysis system 9 comprising an ESI ion source 10, a DMS 11, an ion guide 12, various optical elements, a first mass filter 20, an election-ion reaction device 21, a collision cell 22 and a time-of-flight (TOF) analyzer 23 are present. As would be appreciated, various elements of this specific design can be replaced or removed with one or more other elements in accordance with the present teachings. For example, while a TOF analyzer 23 is specifically described, it should be appreciated that any sort of mass analyzer can be substituted at this location with expected differences in performance, such as a quadrupole rod set acting as a second mass filter. In other embodiments, the TOF analyzer can be replaced with an ion trap. In addition, optical elements present for allowing the transfer of ions from stage to stage can be removed or replaced so long as the ion transport through the device is maintained.

The DMS device 11 consists of two parallel planar electrodes 30 along an ion path 31 through which ions flow. The electrodes can be configured in a manner to introduce via an AC voltage source 32, a separation voltage, to the electrodes 30. The separation voltage comprises an asymmetric voltage waveform 33 in which differing voltages are applied as a function of time, while the total integration of voltages over one period is zero. Overall, ions travelling through the DMS cell 11 generally attain a sawtooth shaped trajectory that is oriented toward one of the two electrodes. To correct these ions' trajectories to attain a path that is on-axis with acceptance into the MS orifice, application via a DC voltage source 34, a compensation voltage (CoV), is employed to bring ions successfully into the MS. By tailoring the SV and CoV combinations, ions containing specific DMS properties can be made to pass through the DMS device while other ions are made to contact the electrodes.

Figure 5:
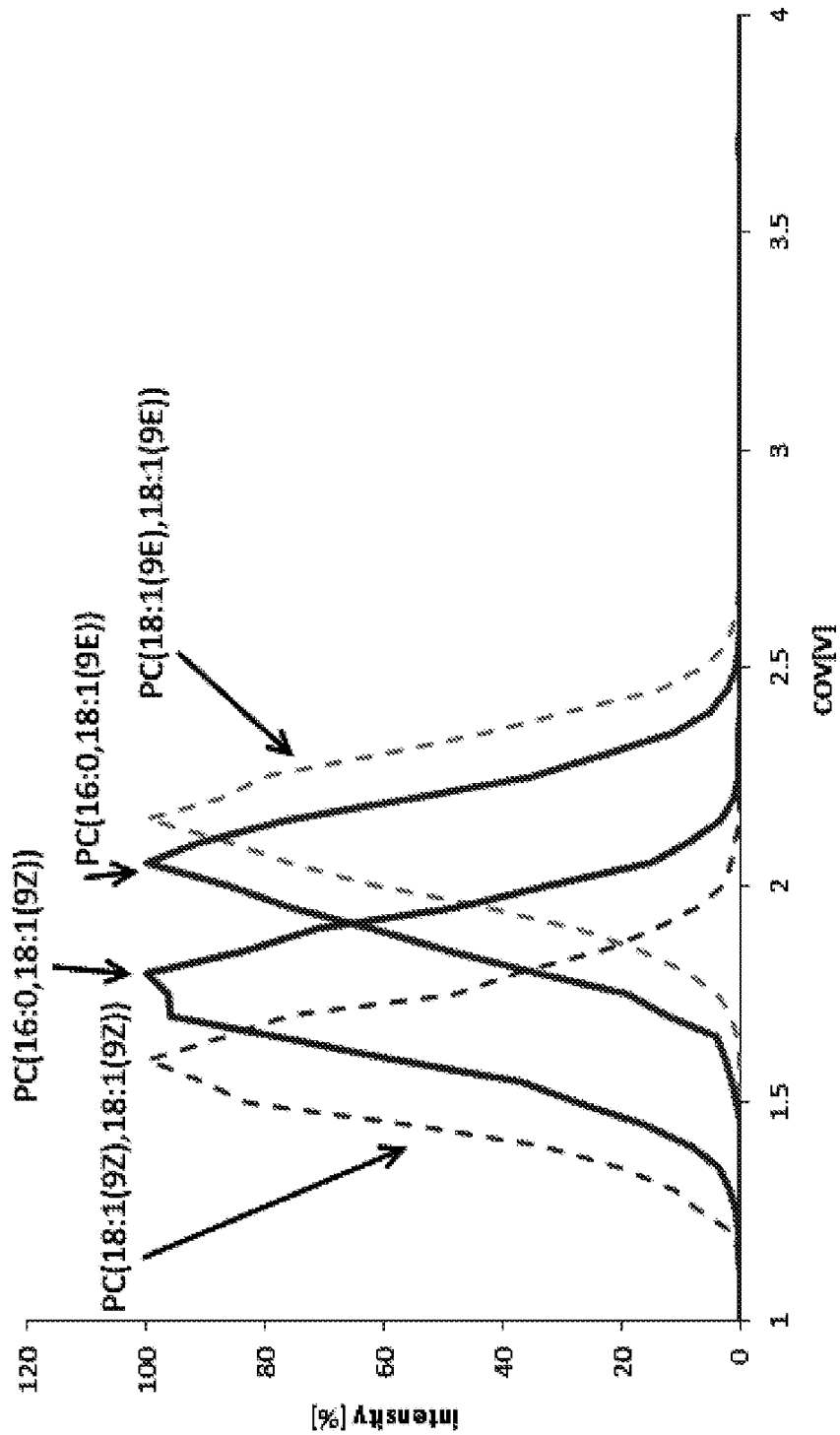
FIG. 5 depicts the separation of cis and trans PCs with saturated/unsaturated acyl chains utilizing DMS.

FIG. 5 shows the separation performed utilizing a SCIEX SelexION™ DMS on cis and trans PCs with saturated and unsaturated acyl chains. The separation voltage was fixed at 3900V and the compensation voltage was scanned. DMS separation was found to be better for samples that contained two unsaturated acyl groups than for PCs with mixed saturated/unsaturated chains. Nevertheless, cis/trans separation using the within teachings can be improved with DMS for samples containing mixed saturated and unsaturated acyl chains.

Figure 6:
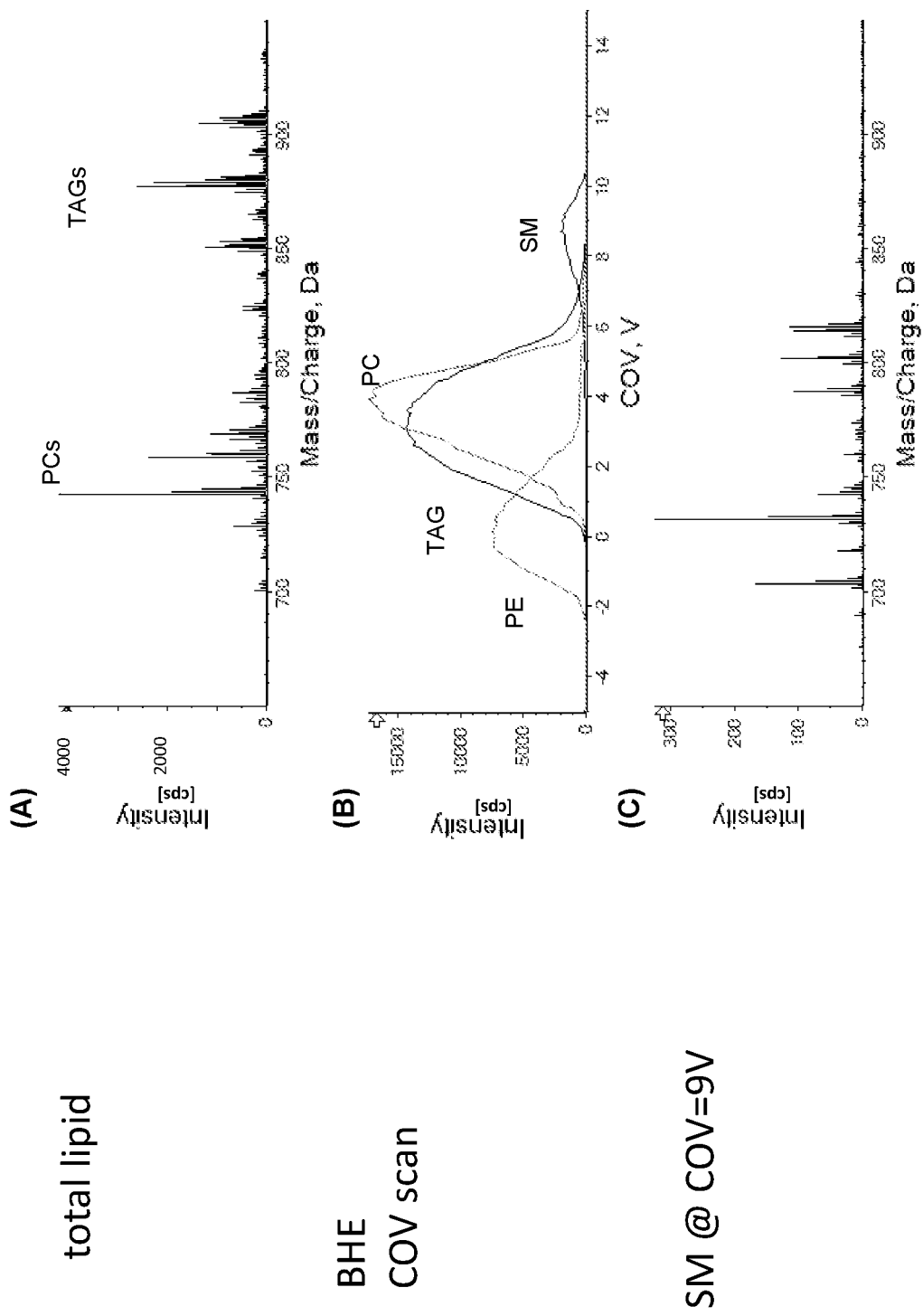
FIG. 6 depicts a series of three plots that represent the positive-mode ESI-MS spectrum of Bovine Heart Extract without any separation of the lipid classes provided (A), a DMS ionogram of the separation of various lipid classes (B) and a positive-mode ESI-MS spectrum of sphingomyelin lipids after isolation of this lipid class using DMS (C).

FIG. 6 (A) shows a total lipid mass spectrum of bovine heart extract (BHE) that contains multiple types of lipid compounds. FIG. 6 (B) depicts a DMS CoV scan of a BHE extract showing that different lipid classes may be separated from one another based upon their characteristic CoVs. FIG. 6 (C) shows a mass spectrum of the same BHE sample subjected to DMS separation with the CoV set at +9V to analyze the sphingomyelin (SM) class of lipids selectively.

While it is conceived that there are numerous methods of utilizing this information to determine the ratio of isomers in a mixture, exemplary methods described herein should be construed as being non-limiting.

Standard sphingomyelin (SM), SM(d18:1, 12:0) and a phosphocholine (PC) share a common head group and when subjected to an electron-ion reaction and subsequent mass analysis exhibit a peak at m/z 184. This fragment is typically used as a diagnostic peak to reveal the presence of either SM or PC lipids. However, it has been found that it is possible to differentiate between either the phosphatidyl or sphingosine backbones by analyzing other peaks of the resulting EIEIO mass spectra. For example, SMs fragment by EIEIO to provide additional diagnostic fragments at m/z 225.1 and m/z 253.095; these diagnostic peaks differ from those produced by PCs, which yield fragments at m/z 224.1 and m/z 226.08. Preferably, when conducting EIEIO analysis of SMs, the electron energy should be set at about 10 eV, which provides diagnostic peaks with optimal intensity.

Figure 7:
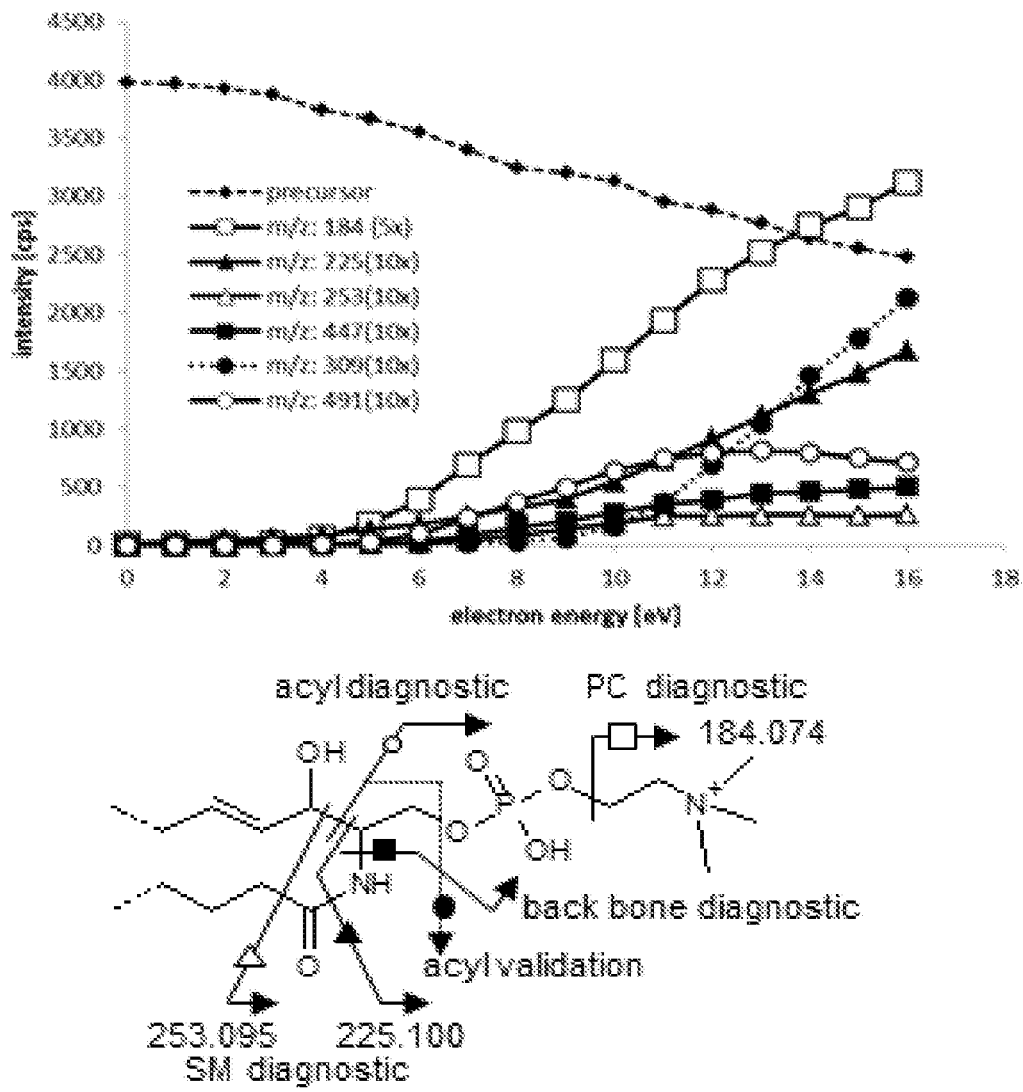
FIG. 7 shows a plot of signal intensity of diagnostic peaks for sphingomyelins (SMs) based on electron energy and fragmentation positions.

In addition, dissociation of the bonds around the head group, the back bone and the acyl shown in FIG. 7 occurs in many SMs and may also be used as diagnostics peaks. In particular, the diagnostic peak at m/z 447.311 (i.e., m/z 449.326−2H) and also m/z 407.264 may also be used. Furthermore, the acyl chain validation peak at m/z 225.269 may also be used.

At lower energies, some of the diagnostic peaks become less sensitive, whereas at higher energies (e.g., >11 eV), background noise increases drastically as background molecules in the ion reaction cell can be ionized by the more energetic beam of electrons. This background noise interferes with the diagnostic peaks associated with the head group.

Depending on the acyl chain length of the sphingomyelin differing diagnostic fragment ions can be selected according to the following table:

| Lipid Class Diagnostic Peaks | | |
|---|---|---|
| PC/SM Head Group | m/z 184.074 | |
| Sphingomyelin (SM) | m/z 225.100 | m/z 253.095 |

| Back Bone Diagnostic | |
| --- | --- |
| D16:1 | m/z 419.280 |
| D17:1 | m/z 433.296 |
| D18:1 | m/z 447.311 |
| D19:1 | m/z 461.327 |
| D20:1 | m/z 475.343 |
| Sphingamine | +2.0156 |
| Sphingadiene | −2.0156 |

Additional backbone acyl diagnostic and validation peaks can be determined by Formulas 2 and 3:

$$[\text{acyl diagnostic}] = 239.205 + (C+2H)*(\text{acyl chain length}) - 2H*(\text{number of double bond}) \quad (2)$$

$$[\text{acyl validation}] = 57.144 + (C+2H)*(\text{acyl chain length}) - 2H*(\text{number of double bond}) \quad (3)$$

Exemplary diagnostic and validation peaks using these formulas depending on the number of the double bonds present and can be calculated according to the following table:

| acyl | acyl diagnostic | acyl validation |
| --- | --- | --- |
| 16 | 463.292-2H*n | 281.231-2H*n |
| 17 | 477.297-2H*n | 295.236-2H*n |
| 18 | 491.302-2H*n | 309.241-2H*n |
| 19 | 505.308-2H*n | 323.247-2H*n |
| 20 | 519.313-2H*n | 337.252-2H*n |
| 21 | 533.319-2H*n | 351.258-2H*n |
| 22 | 547.324-2H*n | 365.263-2H*n |
| 23 | 561.329-2H*n | 379.268-2H*n |
| 24 | 575.335-2H*n | 393.274-2H*n |
| 25 | 589.34-2H*n | 407.279-2H*n |
| 26 | 603.346-2H*n | 421.285-2H*n | n = number of double bonds,
2H = 2.0156

By reviewing the mass spectra and noting the presence of characteristic peaks, the length of the chain and number of double bonds present can be determined. The location of the double bond can be determined in accordance with the teachings provided in WO 2015/189749. The orientation of any double bond found to be present can be determined in accordance with the present teachings with appropriate modification.

While the within teachings may be used to detect preferentially the presence of double bonds in the chains of SM-type compounds, it should be appreciated that the analyses described herein are useful for the detection of double bonds, and can be utilized for example, in a non-limiting way to determine a molecule's head group or the presence and types of any chains. Exemplary and non-limiting types of compounds capable of analysis by the within teachings, include sphinganine (no carbon-carbon double bonds), sphingosine (contains one carbon-carbon double bond) and/or spingadiene (two carbon-carbon double bonds).

The triacylglycerol (TAG) class of lipids are representative of edible dietary fats, the determination of individual structures of which is important in developing the pathophysiology of the lipid molecular species. In addition, the potential adulteration of some more expensive forms of edible oils by cheaper forms can be assessed by analytical techniques capable of characterizing the TAG content. TAGS are generally described as containing a glycerol backbone to which three esterified fatty acid chains are attached. In accordance with the present disclosure, analysis of TAGS is included within the present teachings through which detailed structural analysis of the molecule can be obtained, including fatty acid composition, regioisomer identification, double bond position, and/or cis/trans configuration.

It has been found that analysis of TAG molecules subjected to electron-ion reactions provides more specific information when it is complexed with an alkaline metal ion prior to electron exposure than when it is protonated or ammoniated. For example, use of sodium ions from added sodium acetate provides more sequence information via EIEIO than for ammoniated TAGS provided by solutions prepared with dichloromethane:methanol (1:1) with ammonium acetate.

Figure 8:
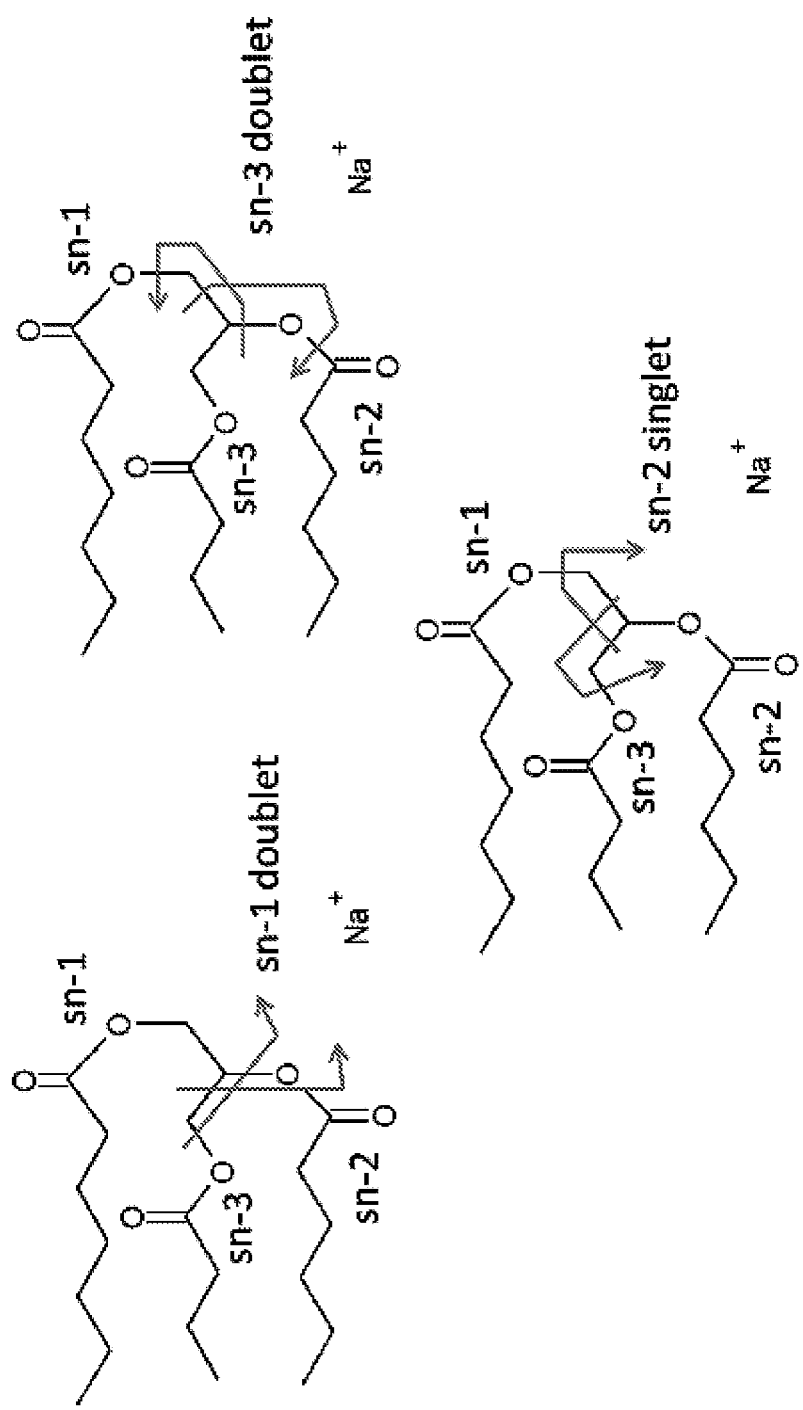
FIG. 8 depicts fragmentation positions for various TAG compounds.

It has been found that after EIEIO fragmentation, a mass spectra of TAG species can have sn-1,3 doublets that are produced by dual acyl chain loss during the fragmentation step which thereby produces acyl chain specificity at the sn-1 and sn-3 positions. The sn-2 singlet is produced during the dual acyl chain loss during fragmentation which provides the acyl chain specificity at the sn-2 position. FIG. 8 demonstrates the structure of a TAG species and EIEIO fragmentation positions. FIG. 31 shows sodiated diagnostic peak lists for TAGs of various chain lengths.

In some embodiments of the present teachings, both singly and doubly charged lipid cations can be utilized. Quadrupole selection and subsequent EID of [M+H]+ and ECD of [M+2H]2+ ions from various lipids resulted in product ions representing dissociation of the precursors. ECD (electron energy: 0-3 eV on doubly charged ions) gave glycan backbone information mainly and EID (10 eV on singly charged ions) gave lipid chain information. In some instances, ionization of certain types of lipids produced double charged species that underwent ECD at electron energies of approximately 1 eV.

In accordance with the present teachings, a reaction apparatus configured according to some embodiments may operate in various modes of operation. In a continuous mode of operation, a stream of ions is introduced continuously into the reaction apparatus at one end and electrons are introduced into the reaction apparatus in a stream that is orthogonal to the stream of ions. Gates situated at the entrance and exit of both the ion pathway and the electron pathway are continuously open. Upon interaction of the ions with the electrons, some of the ions undergo EID or EIEIO and fragment. The product ions which include the fragmented portions, as well as unfragmented precursor ions are then continuously extracted from the reaction apparatus to be subsequently processed and analyzed using an ion detector.

In a semi-continuous mode, the apparatus is configured such that the entrance gate of the ion pathway is continuously open, whereas the exit gate of the ion pathway switches between an open and closed position. The entrance gate for the electron pathway can be opened continuously. When the exit gate of the ion pathway is in a closed position, ions are unable to exit the apparatus through the exit gate and an accumulation of ions takes place within the apparatus. Electrons which are continuously entering the apparatus orthogonally to the incoming ion stream interact with the ions as they accumulate, some of the ions undergoing EID or EIEIO to fragment. Once a sufficient amount of time has passed, the exit gate of the ion pathway is then opened to allow a removal of the product ions and unreacted ions that have accumulated. These exiting ions can then be further processed and/or manipulated in subsequent stages and/or analyzed using an ion detector.

In trapping (or "batch") mode the apparatus is utilized in a manner in which the entrance and exit gates are operated in a fashion to allow ions into the apparatus in a non-continuous mode. Entrance gate of the ion pathway is open and exit gate of the ion pathway is closed and ions are transmitted through the entrance gate into the apparatus. During this time period, entrance gate of the electron pathway is closed. Once a sufficient number of ions are accumulated within the apparatus, the entrance gate of the ion pathway is closed and entrance gate to the electron pathway is opened allowing electrons to enter into the apparatus where they can interact with the accumulated ions and cause a dissociation reaction (e.g., ECD, EID, EIEIO, etc.) to fragment the ions. Once a sufficient period of time has passed for the reaction, the electron entrance gate can be closed or the electron beam can be turned off and the exit gate of the ion pathway is opened to allow extraction of the fragmented product ions or unreacted precursor ions which can then be further processed and/or manipulated and/or analyzed using an ion detector. The duration of time in which the ion exit gate is closed and in which the ions interact with the electrons can be pre-determined as a function of the charge state of the original precursor ions, or can set manually based on experience.

The apparatus may be integrated into a mass spectrometer or tandem mass spectrometer as known to those having ordinary skill in the art. A non-limiting example of a mass spectrometer in which the present teachings can be incorporated is a quadrupole time-of-flight mass spectrometer. The apparatus may be used to analyze various types of samples dissociated using techniques described herein, including samples containing or suspected of containing lipid molecules.

Figure 32:
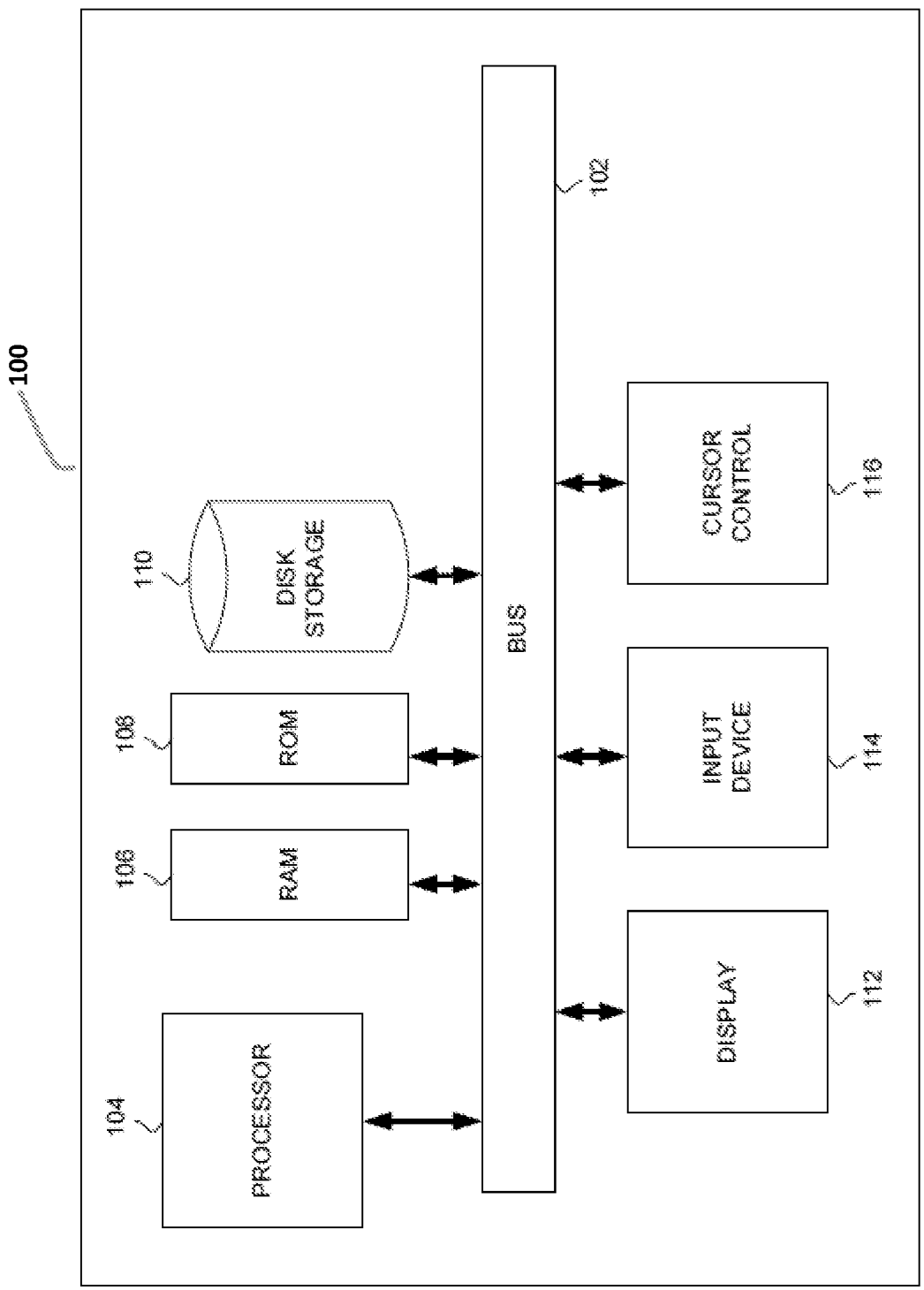
FIG. 32 is a block diagram that illustrates a computer system, on which certain embodiments of the present teachings may be implemented.

FIG. 32 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102 for storing instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein. Alternatively hard-wired circuitry may be used in place of or in combination with software instructions to implement the present teachings. Thus implementations of the present teachings are not limited to any specific combination of hardware circuitry and software.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media include, for example, a floppy disk, a flexible disk, hard disk, magnetic tape, or any other magnetic medium, a CD-ROM, digital video disc (DVD), a Blu-ray Disc, any other optical medium, a thumb drive, a memory card, a RAM, PROM, and EPROM, a FLASHEPROM, any other memory chip or cartridge, or any other tangible medium from which a computer can read.

Various forms of computer readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

In accordance with various embodiments, the computer system may be used to operate and/or control various aspects of the system herein described. In preferred embodiments, the computer is utilized to operate and/or control all aspects of the system and is configured to receive and transmit data to the various components. In some embodiments, the computer system comprises a processor that is in communication with a mass spectrometer that comprises an ion-electron reaction device and a mass analyzer, the processor functions to control various aspects of the mass spectrometer including the ion-electron reaction device, such as an ECD device, and various mass filters and/or analyzers. The process may instruct the ion-election reaction device to conduct an ion-electron reaction between an ionized lipid containing a carbon-carbon double bond and electrons that causes the production of two or more product ions. The processor may also receive an intensity for each of the two or more product ions from the mass spectrometer. The processor may also identify a grouping of the two or more product ions and their associated intensities that is characteristic of a carbon-carbon single bond situated next to said carbon-carbon double bond, at least one or the two or more product ions being characteristic of a non-radical fragment species and another of the two or more product ions being characteristic of a radical species. The processor may also determine a ratio of the intensities of said non-radical fragment species to said radical species. The process may also determine the cis/trans orientation of the carbon-carbon double bond based on said ratio.

In various aspects, the instructions carried out by the process described herein may be stored on a computer readable medium.

EXAMPLES

The applicants' teachings can be even more fully understood with reference to the following examples and data presented in the Figures, which demonstrate the analysis of isomeric lipids present in a sample and/or the location and/or configuration of double bonds in analyzed molecules by analyzing dissociated fragments (i.e., fragment ions) dissociated in accordance with various aspects of the teachings herein. Other embodiments of the applicants' teachings will be apparent to those skilled in the art from consideration of the present specification and practice of the present teachings disclosed herein. It is intended that these examples be considered as exemplary only.

Example 1: Double Bond Location

Figure 9:
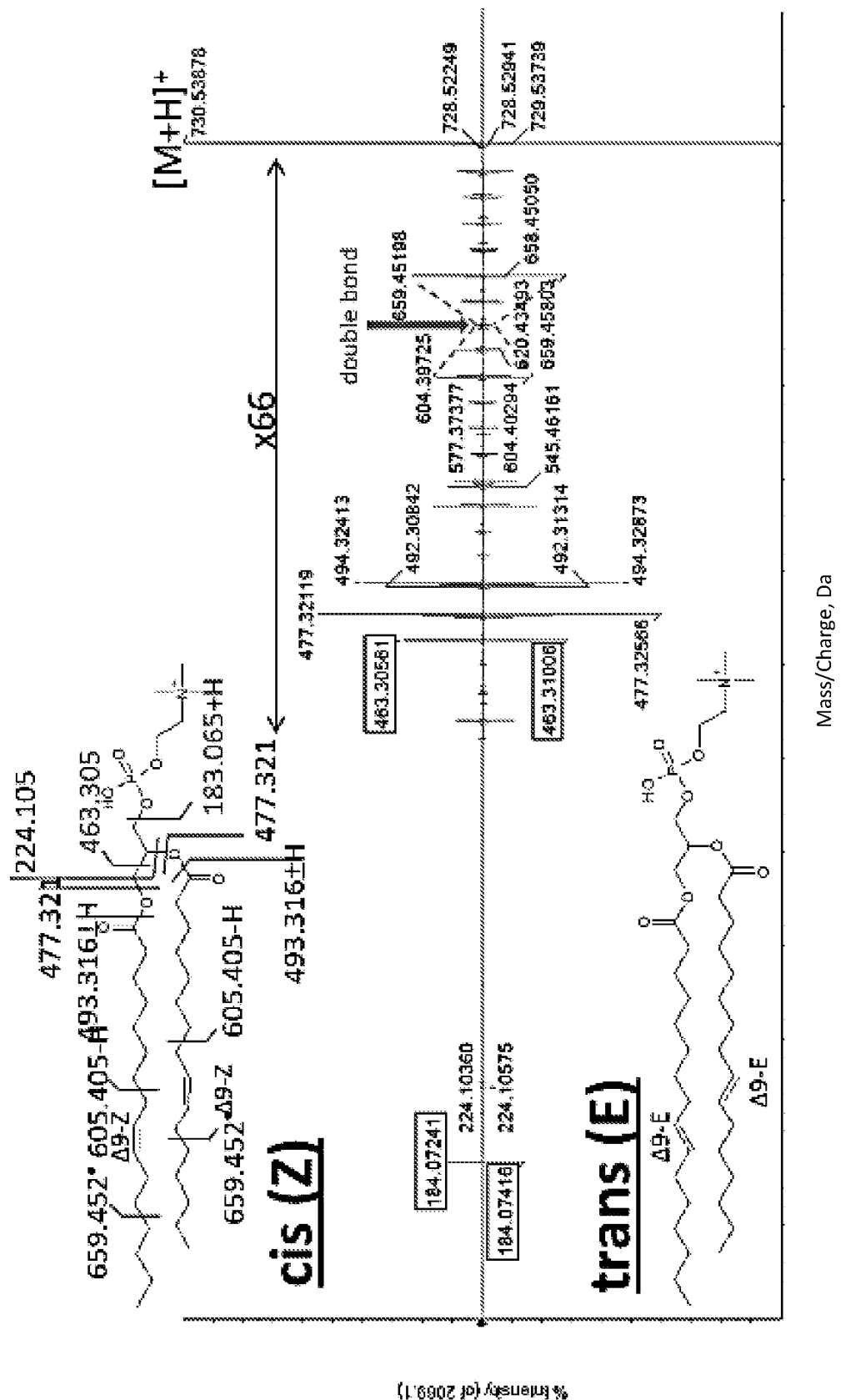
FIGS. 9 and 10 depict a comparison of mass spectra between cis and trans forms of a PC lipid.

As a non-limiting example, referring to FIG. 9, there is depicted two mass spectra obtained at 8 eV layered over one another such that they share the same x-axis, the top spectra showing the cis-cis orientation of the phosphatidylcholine (PC) (16:1/16:1) with the double bond located at the $9^{th}$ carbon-carbon bond and the bottom spectra showing the trans-trans orientation.

Figure 10:
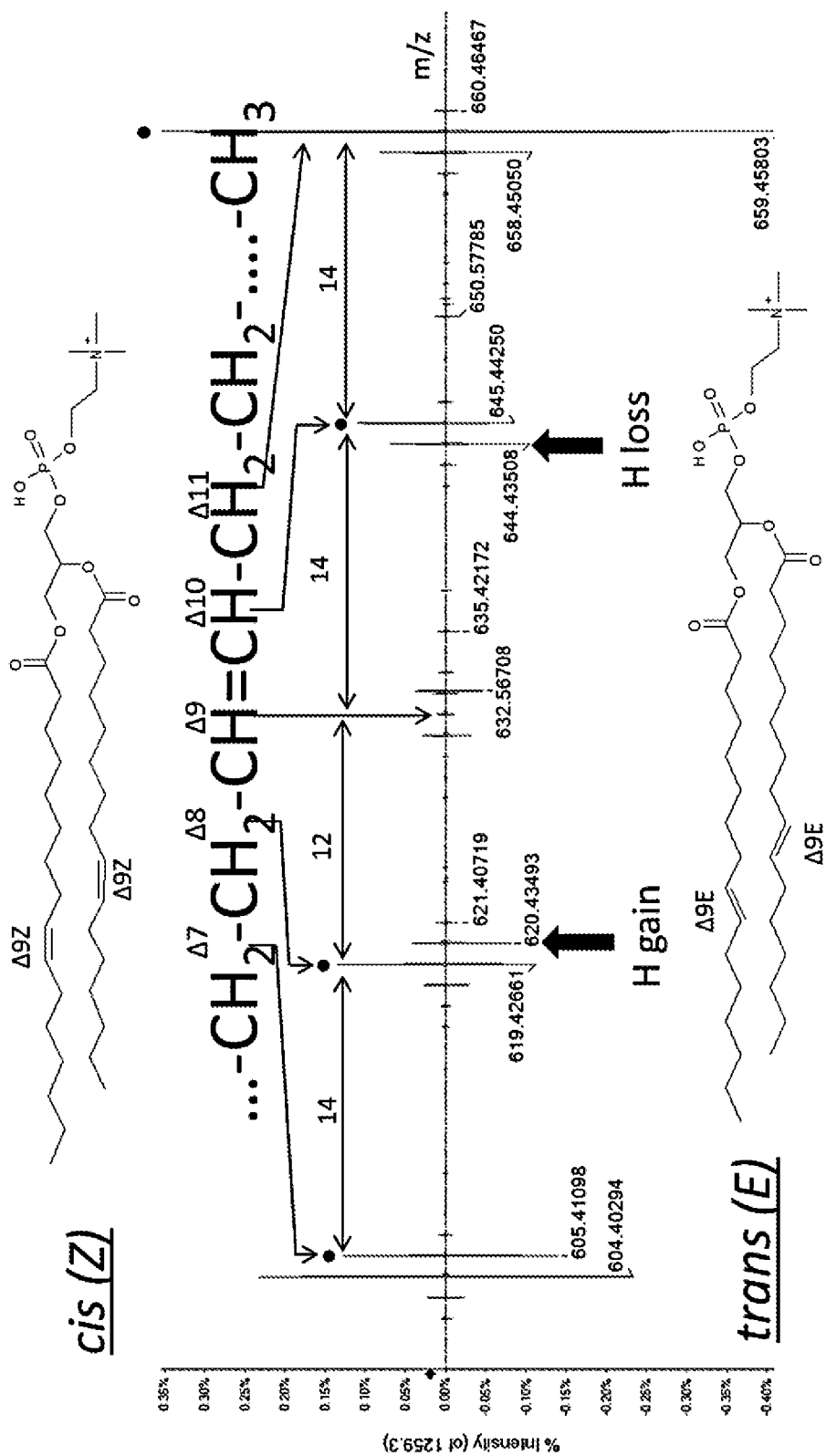

FIG. 10 shows an exploded view of the spectra of FIG. 9 around the double bond location. In accordance with the teachings of WO 2015/189749, peak groupings that are separated by 14 mass units are indicative of a single bond in a chain, whereas a difference of 12 mass units is indicative of the presence of a double bond. The difference of 12 mass units indicates the location of the double bond at the $9^{th}$ position, consistent with the known structure of the compounds.

Example 2: Cis/Trans Orientation

Referring to FIG. 10, the grouping of peaks associated with and characterizing the carbon-carbon bond situated next to the double bond shows a peak intensity difference between the two isomers. Specifically, at the $10^{th}$ carbon-carbon bond position (i.e., the Δ10 position). It was found that the peak intensity with one m/z difference from the radical fragment from this adjacent bond is indicative of the cis or trans orientation of the neighboring double bond. These differences can be determined by normalizing peak ratios utilizing equation 1.

Figure 11:
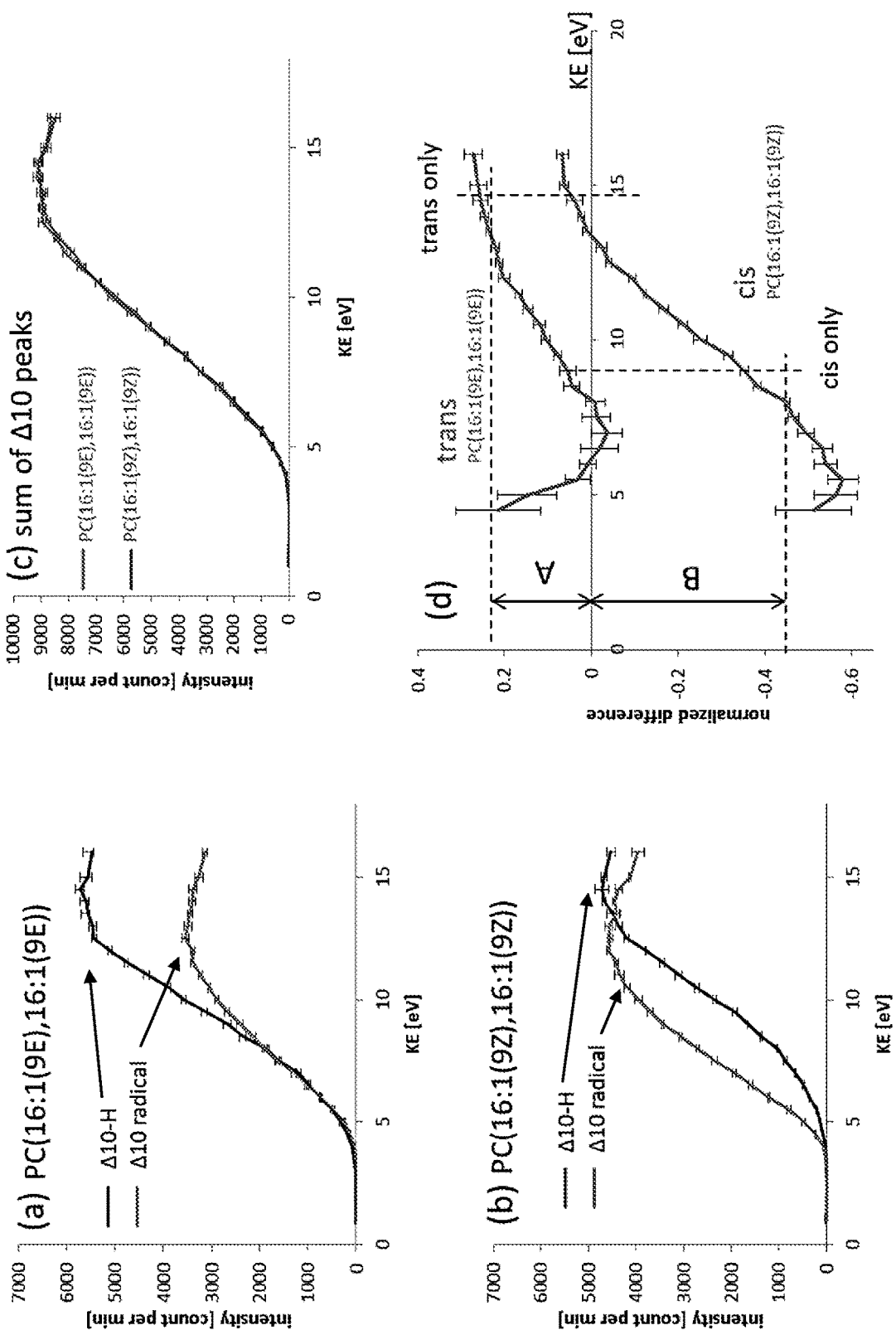
FIG. 11 depicts the electron kinetic energy dependence on the appearance of non-radical and radical fragment peaks at the delta 10 carbon-carbon bond cleavage in PC

Now referring to FIG. 11, there is depicted a series of plots showing peak intensity vs. electron kinetic energy used in the ion-electron reaction for the trans-trans (FIG. 11(a)) and cis-cis (FIG. 11(b)) molecules of PC (16:1, 16:1) containing a carbon-carbon double bond situated at the 49 position. These plots show that, at a given electron kinetic energy (at less than 13 eV), the non-radical peak intensity in a trans-trans orientation of PC (16:1, 16:1) is higher when compared to the intensity of a corresponding cis-cis molecule and that the reverse is the case when considering the peak intensity of the Δ10 radical associated with the carbon-carbon single bond next to the double bond. FIG. 11(c) shows the cumulative intensity of the Δ10 radical and corresponding Δ10 non-radical fragment intensity for each of the cis-cis and trans-trans isomers, showing that the total sum of these fragments for each of the cis-cis and trans-trans is virtually the same. Accordingly, the individual contribution of the Δ10 H to this total will vary depending on whether the molecule is cis-cis or trans-trans and this difference can be utilized to identify the relative presence of each of the isomers in a mixture.

FIG. 11(d) plots the normalized peak intensity calculated using Equation 1 of the pure trans-trans isomer (top) compared to the pure cis-cis isomer (bottom).

FIG. 11(d) shows the normalized difference for the trans-trans and the cis-cis isomers is approximately 0 at electron kinetic energies of 8 and 13 eV, respectively. By obtaining spectra in accordance with the present teachings at an electron kinetic energy of 8 eV and calculating a normalized peak difference, the contribution to peak intensity offered by the trans isomer can be eliminated and the intensity of the cis isomer can be measured. Similarly, by obtaining spectra in accordance with the present teachings at an electron kinetic energy of 13 eV and calculating a normalized peak difference, it is possible to eliminate the contribution to peak intensity by the cis isomer, therefore allowing a determination of the intensity of the trans isomer.

The value of "A" in FIG. 11(d) (approximately +0.22) represents the normalized intensity difference at 13 eV for the pure trans-trans sample. If a sample containing an unknown mixture of trans and cis isomers is analyzed at this energy, the normalized peak intensity should have a value between 0 and A which will depend on the molar ratio between the trans and cis isomers. The ratio of the normalized intensity at 13 eV for the mixture to the normalized intensity of the pure trans isomer will therefore be the molar ratio of the trans isomer in the mixture. The cis ratio can then be determined by being 100%−(trans molar ratio %).

Similarly, the value of "B" in FIG. 11(d) (approximately −0.45) represents the normalized intensity difference at 8 eV for the pure cis-cis sample. If a sample containing an unknown mixture of the trans and cis isomers is analyzed at this energy, the normalized peak intensity should have a value of between 0 and B which depends on the molar ratio between the trans and cis isomers. The ratio of the normalized intensity at 8 eV for the mixture to the normalized intensity of the pure cis isomer will therefore be the molar ratio of the cis isomer in the mixture. The trans ratio can then be determined by being 100%−(cis molar ratio %).

Figure 12:
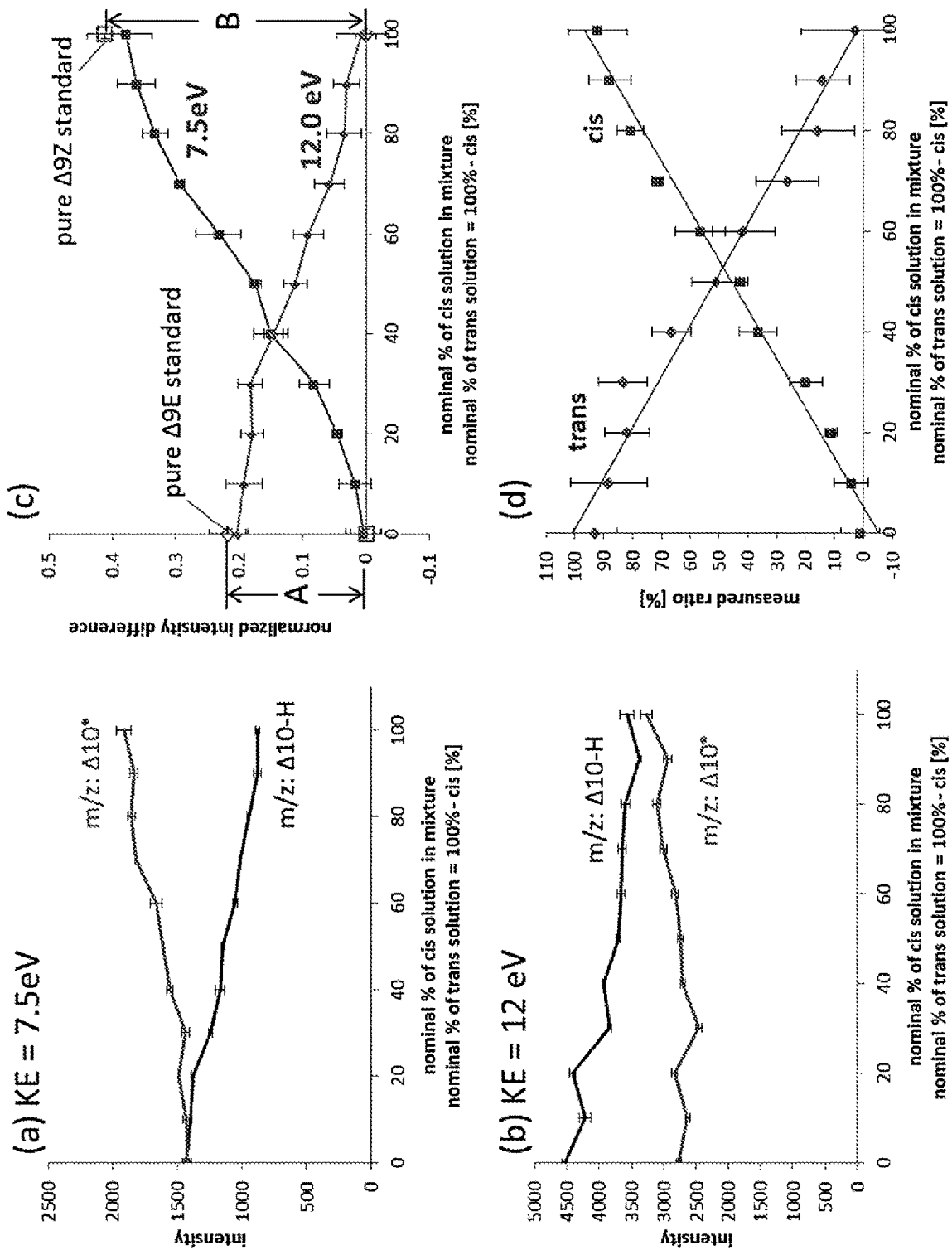
FIG. 12 depicts the experimental observations, electron kinetic energy dependencies, and outcomes of a standard PC cis/trans titration for the determination of the ratios of cis acyl chains and trans acyl chains.
Figure 13:
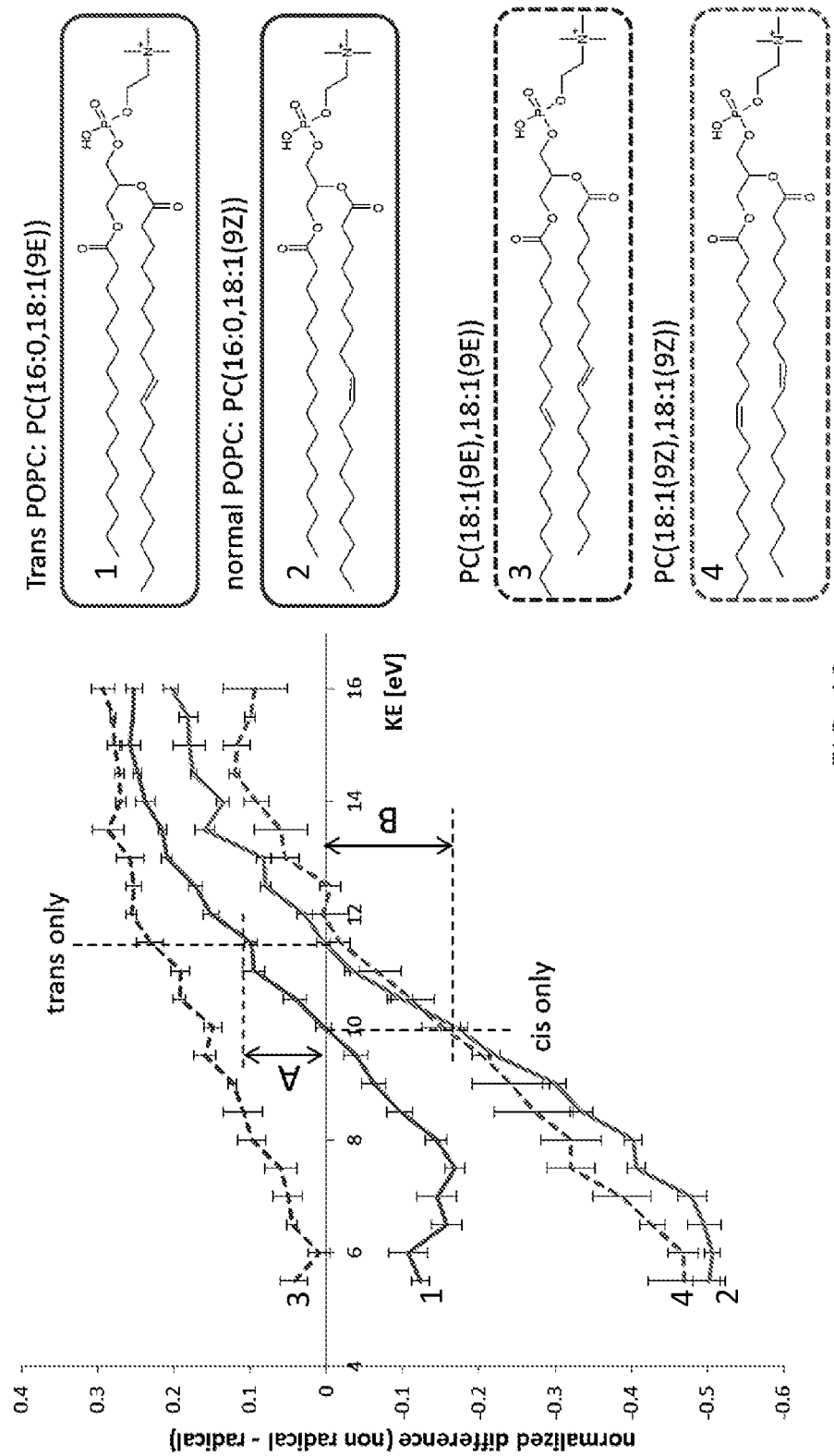
FIG. 13 shows the normalized difference between non-radical and radical peaks of various compounds as a function of electron energy.

Now referring to FIG. 12, plots of the normalized intensity differences for various mixtures of the cis-cis and trans-trans isomers is shown demonstrating the linear relationship FIG. 13 depicts the normalized difference plots as a function of electron kinetic energy for the exemplary compounds. The compound cis-POPC has a saturated acyl group and has a similar electron energy dependence as PC (18:1 (9Z), 18:1 (9Z)). Trans-POPC, which contains an unsaturated trans acyl group, showed an electron kinetic energy profile that was positioned in between the trans-trans isomer and the cis-cis isomer. This suggests that the saturated 16:0 acyl chain showed a similar profile to the cis acyl or saturated acyl pattern and that the unsaturated trans acyl group would show a similar profile to the trans acyl pattern. As depicted for the cis-POPC and trans-POPC molecules, the normalized difference at electron kinetic energies of 10 eV and 11.5 eV are utilized to determine the relative intensity ratios of the cis-POPC and the trans-POPC, respectively.

Figure 14:
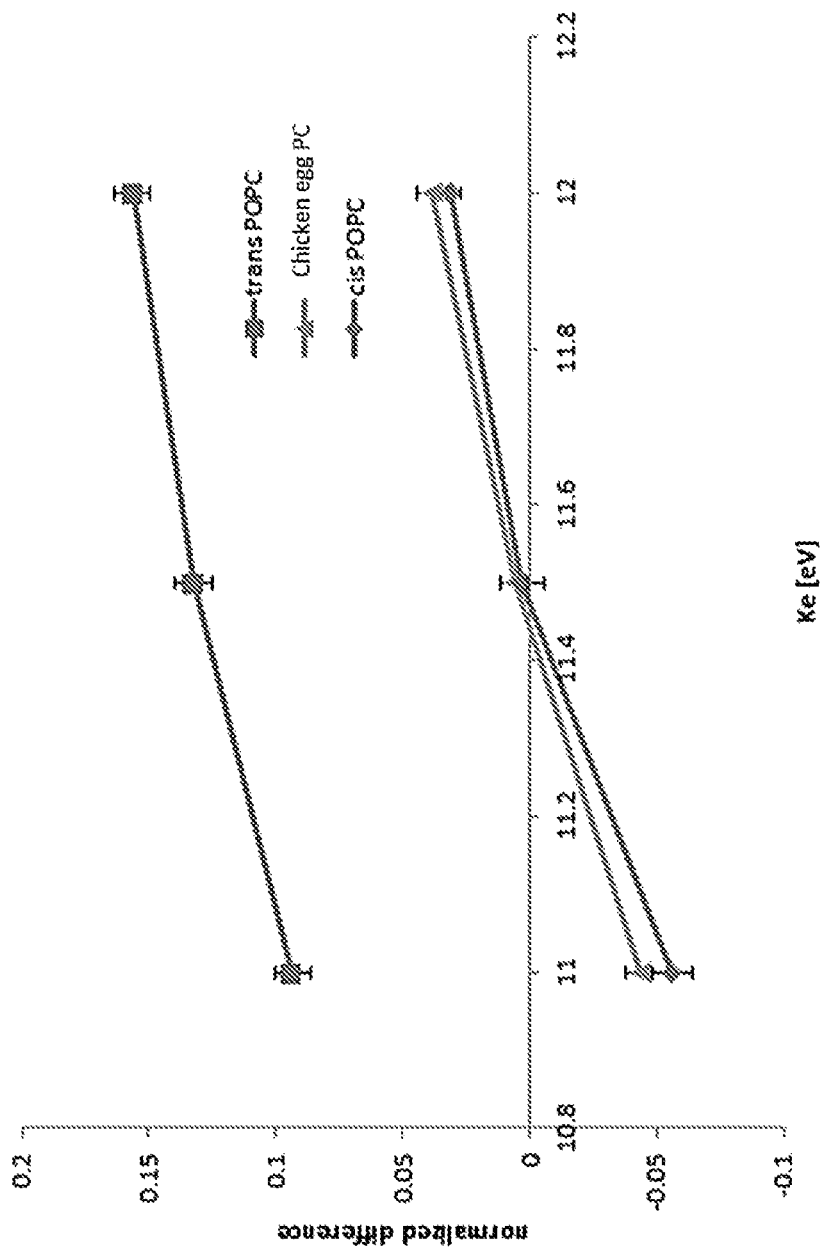
FIG. 14 shows an analysis of a PC extracted from chicken egg compared to trans and cis POPC.

FIG. 14 depicts a series of analysis performed of a grocery store purchased sample of egg showing there to be minimal contamination in the egg yolk of Trans-POPC in the sample.

Example 3: Analysis of Sphingomyelins

A SCIEX TripleTOF 5600 mass spectrometer system was modified, which included a DMS and a branched RF ion reaction cell as depicted in FIG. 4. The DMS (SelexIon™, Sciex) was installed between the ESI source and the vacuum inlet (or orifice plate). The DMS system was optimized to maximize the SM yield using the following conditions, where separation resolution was compromised and TAGS and PCs were not resolved.

ESI Source: +5000V
Modifier: 2-propanol, modifier flow: 162 µL/min
Temperature of DMS region 200 C
DMS resolving gas pressure (DR): 10 psi
Separation voltage (SV): 3900V
Compensation voltage (COV): scanned between −5V to 20 V.

Pre-separation before precursor isolation in the first quadrupole filter (Q1) was utilized because of overlapped contamination of isotopomers (i.e., overlapped species with $^{13}C$ contributions from other lipid classes).

The DMS was used to separate the standard sample SM(d18:1,12:0) and brain SM, egg SM and milk SM because sodiated SMs were contained in the total precursor ions at about a 10% level even though the samples themselves were pure.

The ion reaction cell utilized is consistent with those described in WO2014/191821. For cooling of ions in the device, helium buffer gas was introduced from Q2 cell, where Collision Induced Dissociation takes place. Helium partial pressure in the ion reaction cell was ~3 mTorr, which was the same as pressure in Q2 due to the presence of two large apertures (5 mm in diameter) in IQ2B electrode in addition to the ion path aperture to allow for gas conductance. The electron beam was generated by an yttria coated iridium disk cathode (ES-525, Kimball physics, NH). The cathode was operated at space charge limit of the electron cloud in the ion reaction cell by a bench top direct current (DC) power supply in constant voltage mode. For EIEIO operation, kinetic energy of the electron beam was set to 10 eV by biasing the cathode negatively compared to the branched ion trap electrodes.

The ion reaction cell was operated in simultaneous trapping mode which results in sensitivity higher than in a conventional trapping mode. In this simultaneous trapping mode, ions were irradiated by electron beam during ion loading period into the ECD device, i.e, electron beam was applied when IQ2A lens was set at open and IQ2B lens closed for a period of time of up to 150 ms. Total ions produced by the reaction were injected into Q2 by opening the IQ2B lens for 1 ms in order to mass analyze by the TOF mass analyzer. The ion reaction cell was controlled by an in-house software coded using LabView (National Instruments Co., Austin, Tex.).

Noise due to the presence of residual gas in the electron beam was thought to be a result of hydrocarbons in the mass range of 100-300 Da and vapor of the rough pump oil in the vacuum system. To detect the presence of low levels of some SM species, EI noise spectra was subtracted from the EIEIO spectra. EI noise spectra, which were collected without sample ion flow by closure of the IQ2A lens, were obtained every ~30 min during EIEIO spectrum acquisition. Product ions from SMs were present even after the EI noise subtractions because of the high mass resolution of the TOF-MS analyzer, which is capable of resolving mass differences of a few mDa and is able to differentiate between carbon rich EI noise peaks and SM fragment peaks with oxygen atoms and a phosphorus atom.

For CID operation, two lens electrodes (IQ2A and IQ2B) were continuously opened to allow energetic precursor ions to be introduced into the Q2 collision device. Electron beam in the ECD was discontinued, and nitrogen gas was introduced into Q2 and the ion reaction cell as a collision gas. In order to apply kinetic energy to isolated ions by Q1, all ion path upstream before the IQ2 was biased 60-90 V to the ECD-Q2 assembly.

SM samples were obtained from Avanti Polar Lipids, Inc. (Alabaster, Ala.), and were used without further purification. SM(d18:1,12:0) in chloroform, POPC or PC(16:0,18:1(9Z)) in chloroform and LPC(18:0) in chloroform were used as a known standard sample. Extracted SM from porcine brain (brain SM), bovine milk (milk SM) and chicken (egg SM) in chloroform were used to obtain EIEIO-SM spectra. As an example of SMs in a crude total lipid, total lipid in bovine heart extract (BHE) in chloroform was surveyed. Solvent for all working solution was HPLC-grade dichloromethane (DCM):methanol (MeOH)=50%:50% with ammonium acetate of 10 mM. These solvent and ammonium acetate were purchased from Caledon Laboratory Chemicals (Georgetown, Ontario) and Sigma-Aldrich Canada Co. (Oakville, Ontario), respectively.

Concentrations of working solution were 250 µg/mL for BHE, 100 µg/mL for brain SM, milk SM and egg SM, and 1 µg/mL for the standard SM and PC samples.

Figure 15:
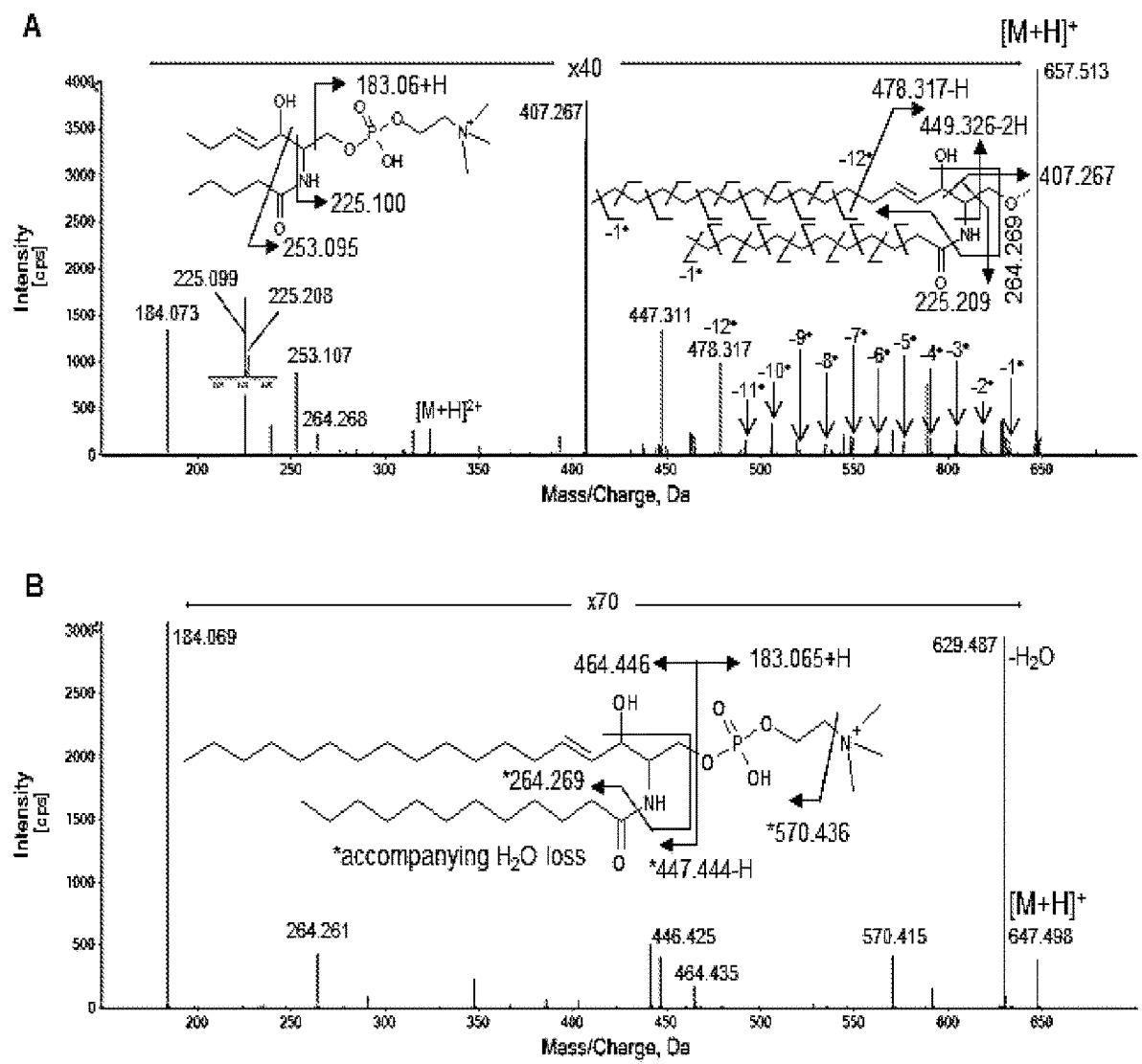
FIG. 15 depicts a dissociation product spectra obtained from EIEIO (A) and by Collision Induced Dissociation (CID) (B).

Referring to FIGS. 15 (A) and (B), there are depicted the mass spectra obtained by EIEIO (A) and a conventional CID analysis (B) of a SM (d18:1,12:0) sample which shows that the EIEIO procedure according to the present teachings provides more detailed fragment information which can be used to characterize the precursor ion structure.

Figure 16:
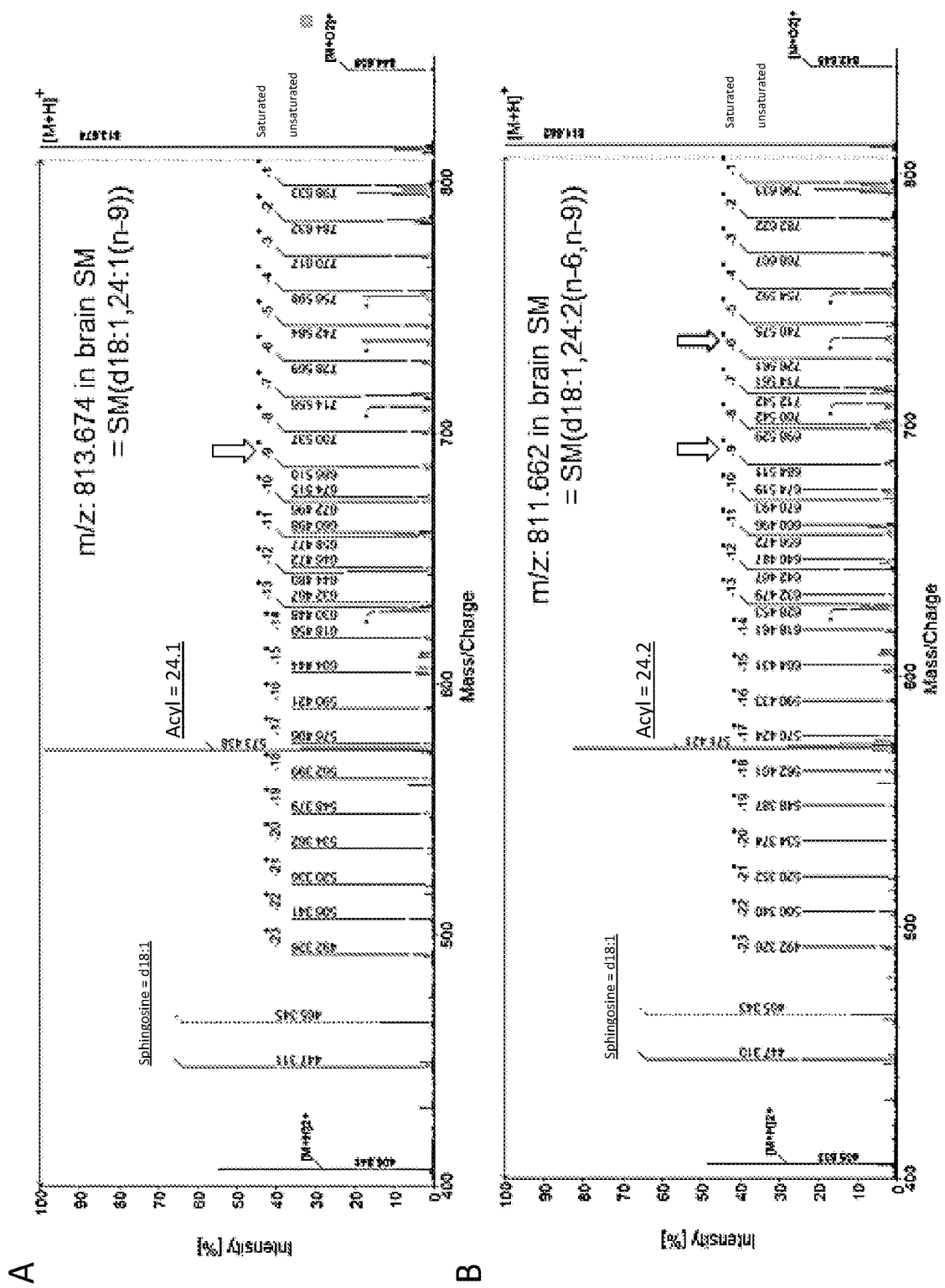
FIG. 16 depicts EIEIO spectra obtained for porcine brain SM showing the presence of a single double-bond (A) and two double bonds (B).

The procedure to determine the presence of the double bond follows the procedure disclosed in WO 2015/189749 which involves the EIEIO reaction of the sample which cleaves the carbon-carbon bonds across the entire chains. Peak spacings between two groups is 14 (carbon+2 hydrogens) for saturated bonds, where the peak spacing is 12 at the locations of the double bonds. This analysis can be performed in cases where a given chain contains more than one double bond. FIG. 16 (A) shows the analysis of a Brain Sphingomyelin sample is Brain SM (d18:1,24:1(−9)). and FIG. 16 (B) shows the analysis of another sample that is SM (d18:1,24:2(−6,−9)) which contains two double bonds. The double bond locations being identified by the presence of the arrows.

Figure 17:
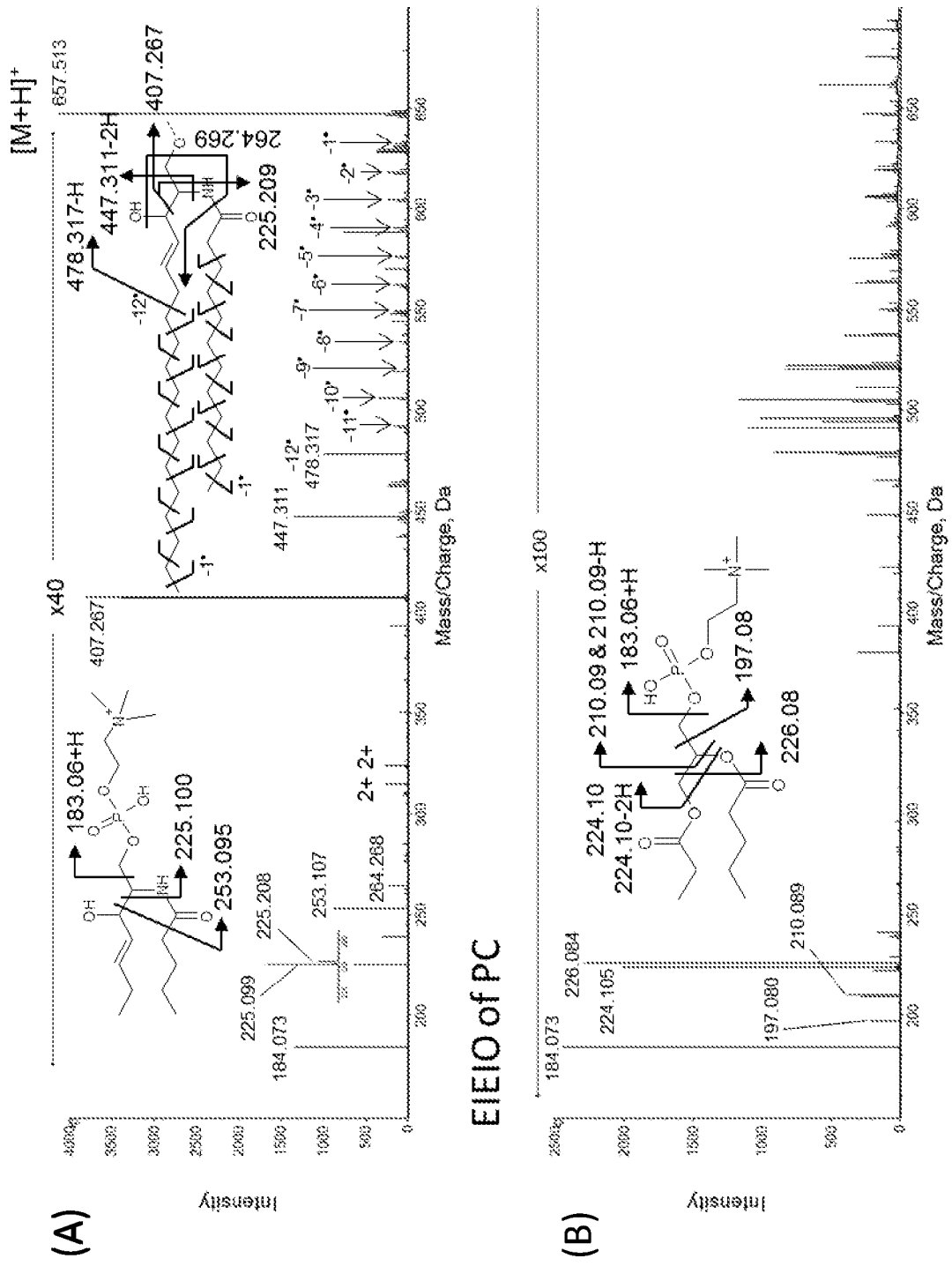
FIG. 17 depicts EIEIO spectra of a sphingomyelin species (A) and of a PC (B).

FIG. 17 (A) shows the mass spectra of an analysis of sphingomyelin SM(d18:1, 12:0) obtained after EIEIO analysis at an electron energy of 10 eV which demonstrates the expected fragmentation pattern showing the presence of characteristic fragment ions at 225 and 253 m/z units together with the head group at 184 m/z. In comparison FIG. 17 (B) shows the mass spectra obtained after EIEIO analysis of PC which shows the same headgroup at m/z=184 but different characteristic fragment ions at 224 and 226 m/z values FIG. 18 shows the MS spectrum of brain SM, and identified SM's in each precursor m/z. The weight constituents (in %) in the tables was calculated from the integrated intensities over the scanned CoV and a calibration curve generated using a standard SM (d18:1,12:0) sample. The % value following each identified SM shows the intensity ratio of the acyl diagnostic peaks in the same precursor m/z as an indicator of expressed ratio.

Figure 20A:
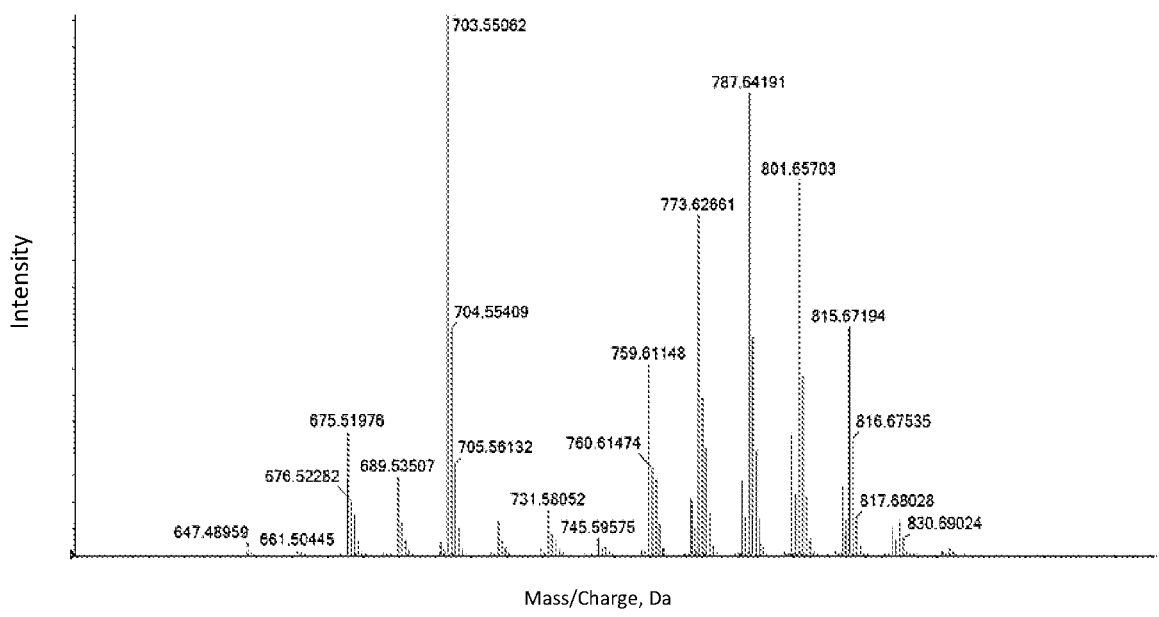
FIGS. 20A and B depicts an MS spectrum of cow milk and a series of identified SM molecules.
Figure 21:
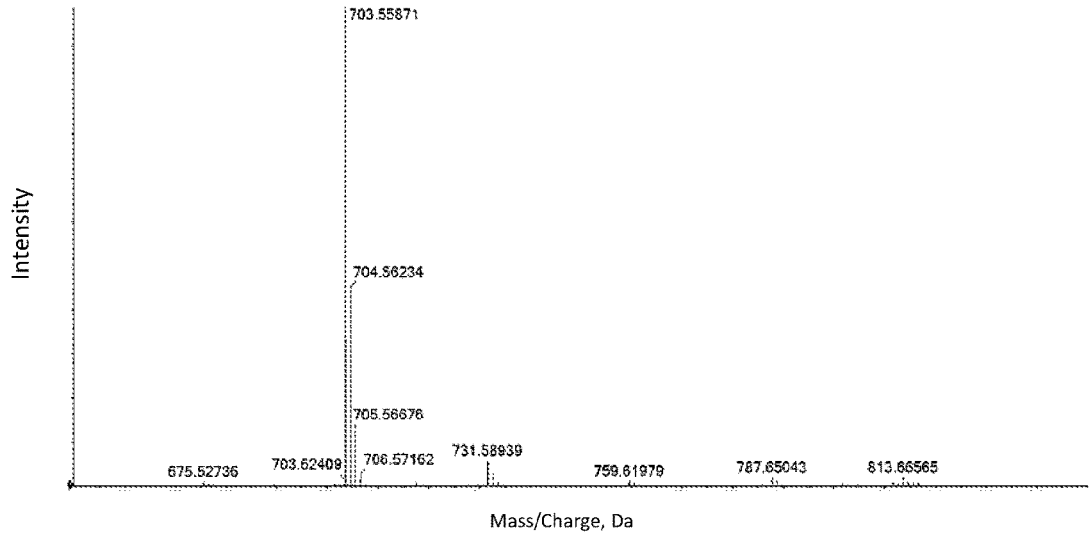
FIG. 21 depicts an MS spectrum of chicken egg and a series of identified SM molecules.

FIG. 19 shows the MS spectrum and identified SM's for a sample of Bovine Heart Extract (BHE) SM. FIGS. 20A and B shows the MS spectrum and identified SM's for a sample of milk SM. FIG. 21 of shows the MS spectrum and identified SM's for a sample of egg SM.

Example 4: Analysis of Tags

Figure 22:
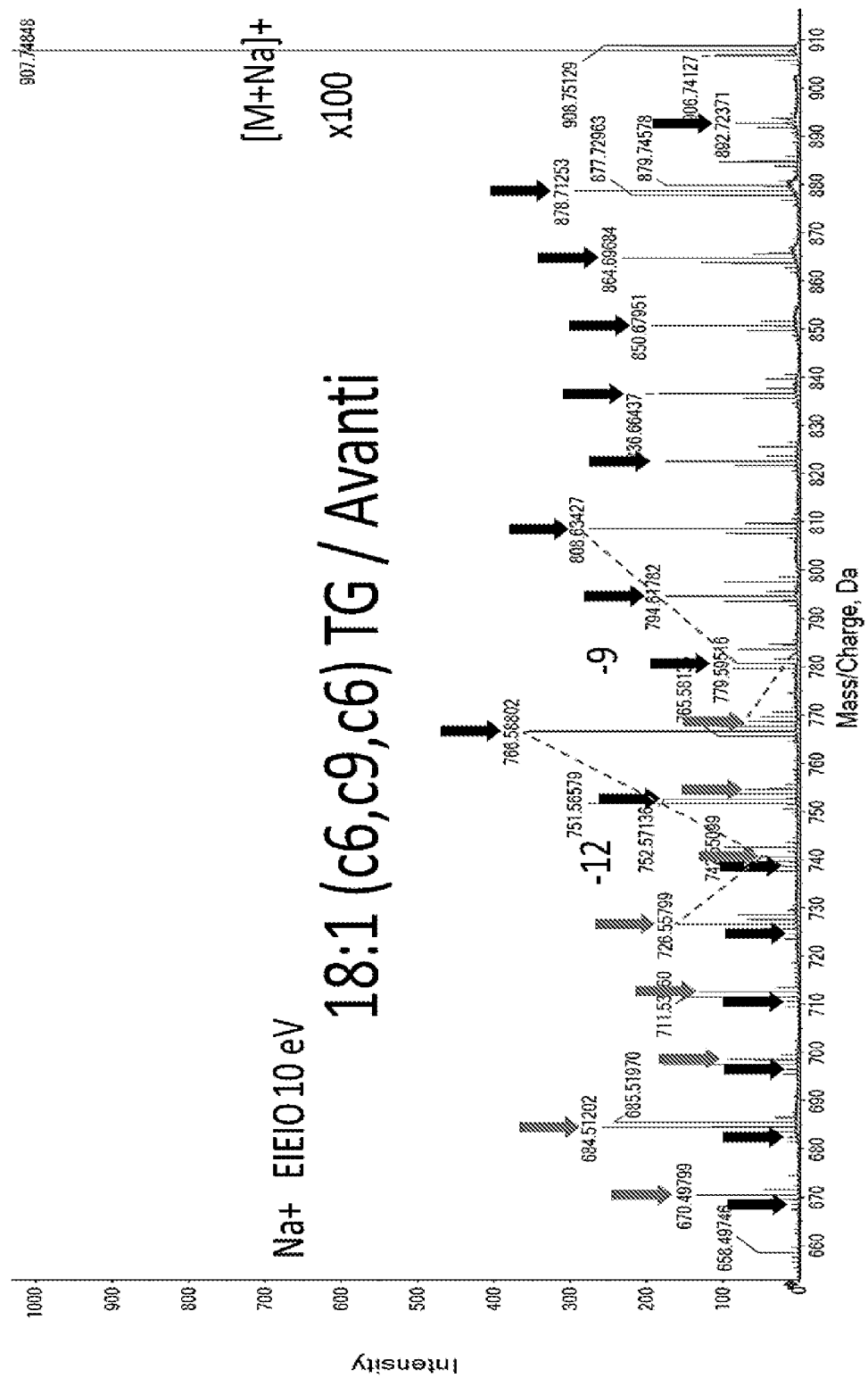
FIG. 22 depicts a double bond analysis of a synthetic TAG sample.

FIG. 22 shows an analysis of a synthetic sample obtained from Avanti Polar Lipids Inc., (Alabaster, Ala.) that contained TG 18:1 (c6,c9,c6). The double bond location is determined in a similar fashion as set out previously for other samples where spacings of 14 m/z units are characteristic of single bonds and spacings of 12 units are characteristic of the presence of a double bond.

Figure 23:
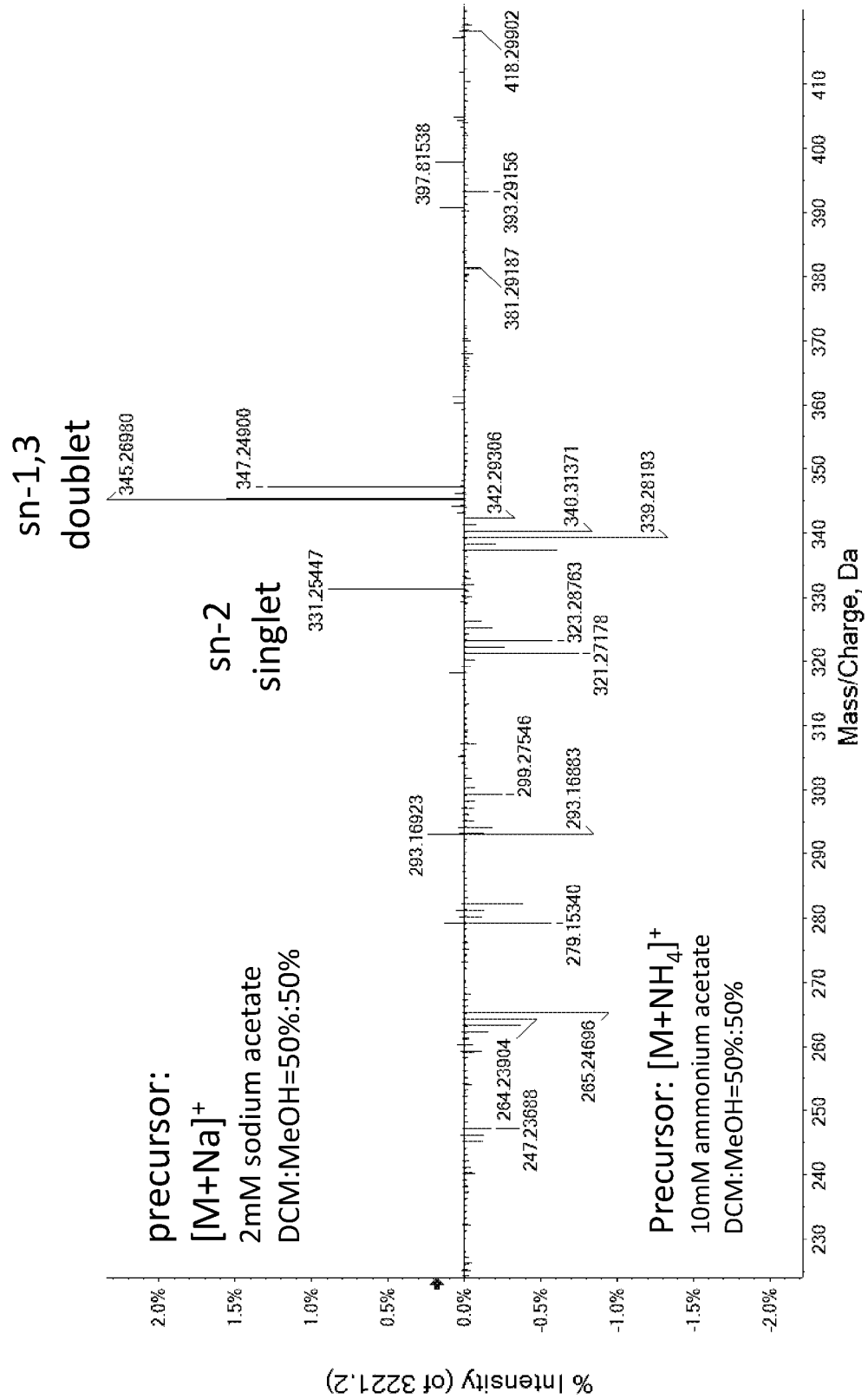
FIG. 23 depicts a comparison of TAG analyses performed using either sodium acetate or ammonium acetate.

FIG. 23 shows a comparison of an EIEIO spectra obtained from an olive oil sample when prepared in a dichloromethanol:methanol (50:50) mixture containing sodium acetate (top) and in a solution wherein ammonium acetate is utilized (bottom). FIG. 24 shows an EIEIO spectra of a mixed molecular species of TAG in an edible oil prepared with sodium acetate. As shown, only the singlet 18:1 TAG species appeared at the sn-2 position. The sodium acetate spectra is shown to exhibit a singlet peak at 331.2 and a doublet peak at 345.3/347.2 representative of the sn-2 and sn-1,3 chains of a TAG present in the sample. The sn-1,3 doublet is produced by dual acyl chain loss during EIEIO, which provides acyl chain specificity at the sn-1 and sn-3 positions. The sn-2 singlet is produced during dual acyl chain loss that results after EIEIO which provides the acyl chain specificity at the sn-2 position.

Figure 26:
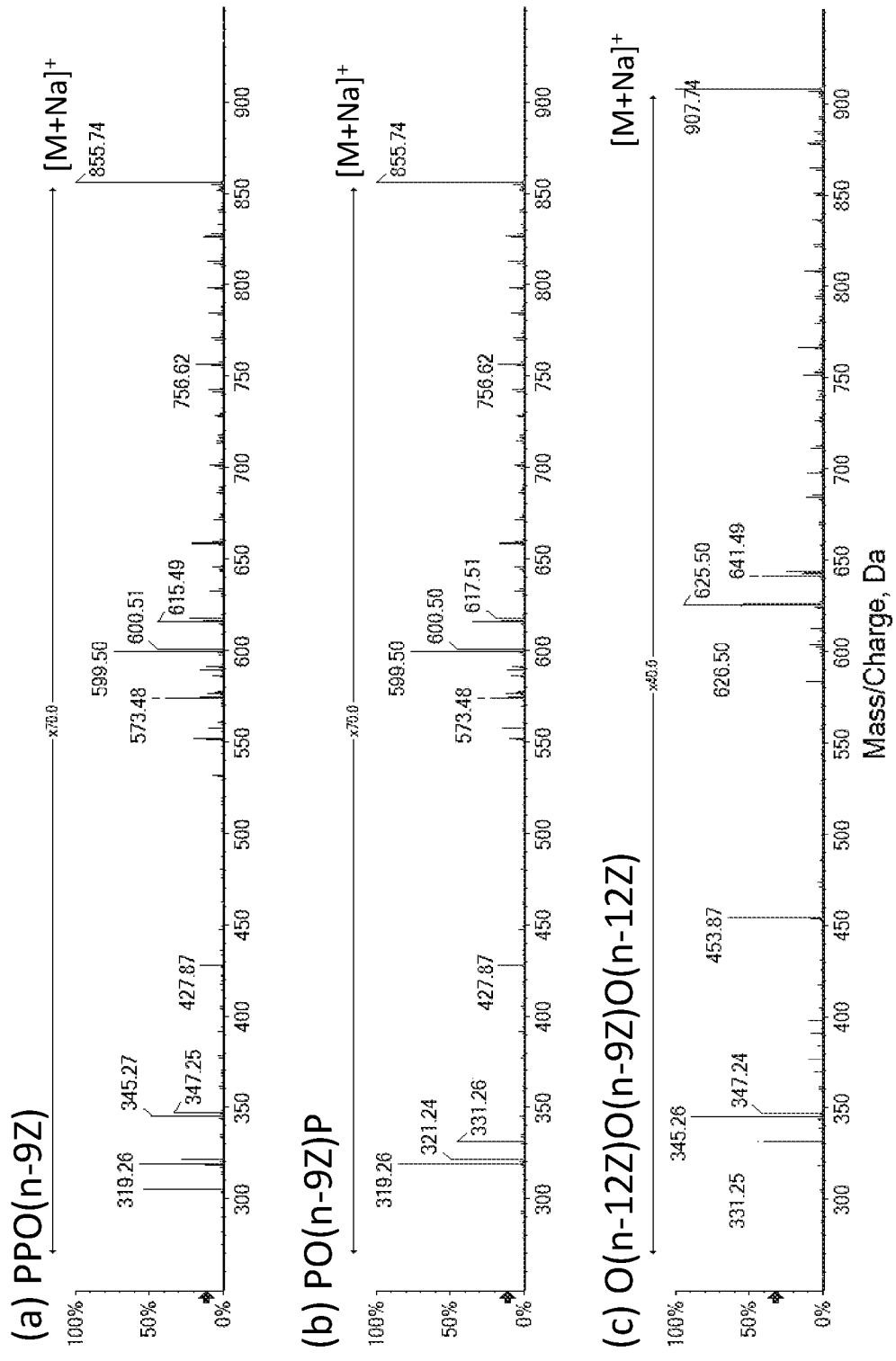
FIG. 26 depicts a series of sodiated full spectra of various TAG structures.

Now referring to FIG. 25, are the chemical structures of three synthetically prepared TAG based lipids comprising PPO (FIG. 25 (a)), POP (FIG. 25 (b)) and OOO (FIG. 25 (c)). A full spectra for each of these compounds is found in FIG. 26(a-c). A more detailed view of each of the spectra between m/z 300 and m/z 350 is depicted in FIG. 27(a-c). These spectra show the various fragment ions associated with the structures.

Figure 28:
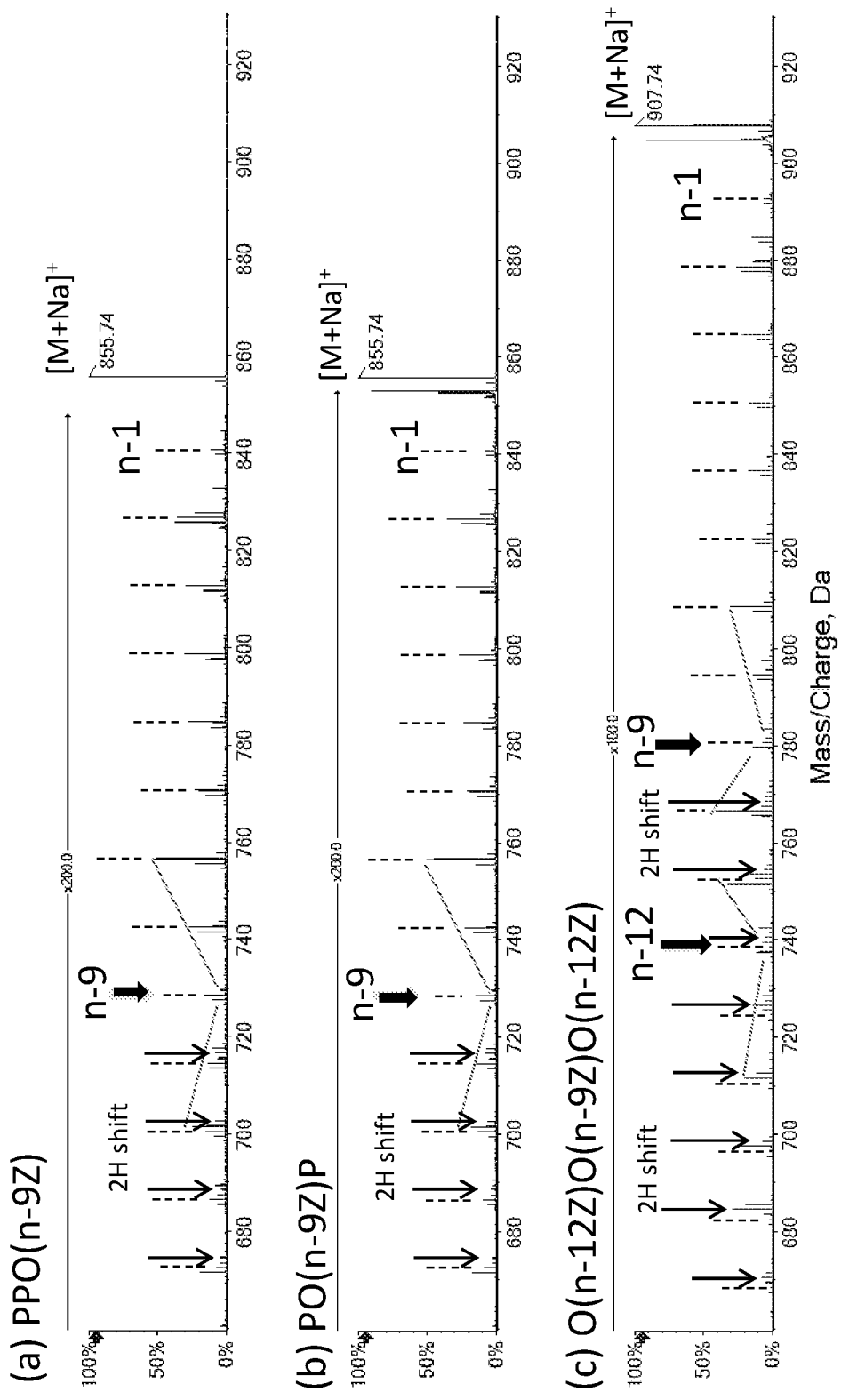
FIG. 28 depicts the identification of double bond location identification in various TAG structures.

Now referring to FIG. 28, the location of the double bond for each of the lipids is demonstrated according to the teachings of WO 2015/189749, herein incorporated by reference where spacings of 14 m/z units are characteristic of single bonds and spacings of 12 m/z units are characteristic of the presence of a double bond Now referring to FIG. 29, there is shown a table of the analysis of a sample of olive oil demonstrating the m/z values and associated TAG molecules that were found to be contained therein.

Now referring to FIG. 30, there is shown a table of the analysis of a sample of omega-3-enriched chicken egg sample showing the m/z values and associated TAG molecules that were found therein.

FIG. 31 depicts a list of diagnostic peaks for mass analysis on TAG species that were analyzed utilizing EIEIO. In particular, peak locations of the dissociation products that vary based on the number of double bonds.

The section headings used herein are for organizational purposes only and are not to be construed as limiting. While the applicants' teachings are described in conjunction with various embodiments, it is not intended that the applicants' teachings be limited to such embodiments. On the contrary, the applicants' teachings encompass various alternatives, modifications, and equivalents, as will be appreciated by those of skill in the art.

What is claimed is:

1. A method for analyzing a sample containing at least one carbon-carbon double-bond containing lipid using a mass spectrometer, the method comprising:
    ionizing the sample to form a plurality of precursor ions,
    fragmenting at least a portion of the plurality of precursor ions into a plurality of fragment ions by irradiating the plurality of precursors ions with electrons; wherein the dissociation reaction is configured to allow distinguishing mass signatures of two isomeric species of said at least one carbon-carbon double-bond containing lipid; and
    detecting at least a portion of the plurality of fragment ions at a detector of the mass spectrometer to form at least one spectrum for mass analysis of the sample, and wherein peak intensities associated with the plurality of fragment ions in said at least one spectrum is used to indicate the cis/trans orientation of said at least one carbon-carbon double bond.

2. The method of claim 1 wherein said electrons have a kinetic energy of about 4 electron volts to about 12 electron volts.

3. The method of claim 1 wherein the peak intensities associated with the plurality of fragment ions are characteristic of a carbon-carbon single bond situated next to said carbon-carbon double-bond.

4. The method of claim 3 wherein the carbon-carbon single bond is situated at a position +1 to the location of the carbon-carbon double bond along a carbon chain of said lipid.

5. The method of claim 3 wherein the peak intensities associated with the plurality of fragment ions comprise a first peak characteristic of non-radical species and a second peak characteristic of a radical fragment species.

6. The method of claim 5 wherein said first peak and said second peak are separated by about 1 Dalton in said spectrum.

7. The method of claim 6 wherein a ratio of said first peak to said second peak is determined and said ratio is used to indicate the cis/trans orientation of said at least one carbon-carbon double bond.

8. The method of claim 7 wherein said ratio is compared to a standard ratio, wherein said standard ratio is obtained by analyzing a standard sample utilizing the same method utilized to calculate said ratio with the exception that said standard sample comprises a lipid species that consists essentially of either a pure cis or pure trans form of said double-bond containing lipid.

9. The method of claim 8 wherein a relative abundance of cis and trans double bonds present in said sample is determined based on said ratio and said standard ratio.

10. The method of claim 1 wherein said plurality of precursor ions are single-charged species.

11. The method of claim 1 wherein the lipid is selected from the group of triacylglycerols and wherein said lipid is complexed with an alkali metal salt prior to ionization.

12. The method of claim 11 wherein the lipid is complexed with an alkali metal salt in a solution of dichloromethane and methanol and optionally wherein the dichloromethane and methanol are mixed in a 50:50 solution by volume.

13. The method of claim 12 wherein the alkali metal salt is a sodium salt and preferably sodium acetate.

14. A system for analyzing a sample containing a carbon-carbon double-bond-containing lipid comprising:
   a mass spectrometer comprising an ion-electron reaction device and a mass analyzer;
   a processor in communication with the mass spectrometer configured to:
   instruct the ion-election reaction device to conduct an ion-electron reaction between an ionized lipid containing a carbon-carbon double bond and electrons that causes the production of two or more product ions;
   receive an intensity for each of the two or more product ions from the mass spectrometer;
   identifies a grouping of the two or more product ions and their associated intensities that is characteristic of a carbon-carbon single bond situated next to said carbon-carbon double bond, at least one or the two or more product ions being characteristic of a non-radical species and another of the two or more product ions being characteristic of a radical species;
   determines a ratio of the intensities of said non-radical species to said radical species; and
   determines the cis/trans orientation of the carbon-carbon double bond based on said ratio.

15. The system of claim 14 wherein the processor identifies a grouping of two or more product ions and their associated intensities that is characteristic of a carbon-carbon double bond, at least one of these characteristic double-bond intensities corresponding to a double-bond radical fragment.

16. The system of claim 15 wherein the double-bond radical fragment and the radical species are separated by 12 Daltons.

17. The system of claim 14 wherein the ionized lipid is singly charged.

18. The system of claim 14 wherein the ionized lipid is doubly charged.

19. A method for analyzing a sample containing or suspected of containing at least one lipid using a mass spectrometer, the lipid being selected from the group of sphingomyelins, the method comprising:
   ionizing the sample to form a plurality of precursor ions;
   performing an electron-ion reaction to fragment at least a portion of the plurality of precursor ions into a plurality of product ions,
   detecting at least a portion of the plurality of product ion species at a detector of the mass spectrometer to form at least one spectrum for mass analysis of the sample and determining the presence of at least one sphingomyelin species in said sample by identifying in said spectrum, diagnostic peaks situated at about m/z 184.075 and about m/z 225.100 or at about m/z 184.075, about m/z 225.100 and about m/z 253.095.

20. The method of claim 19 wherein a DMS separation is performed between the steps of ionizing of the sample and the electron-ion reaction.

* * * * *